United States Patent [19]

Go et al.

[11] Patent Number: 5,696,054
[45] Date of Patent: Dec. 9, 1997

[54] HERBICIDAL 1,3-OXAZIN-4-ONE DERIVATIVES AND INTERMEDIATES THERETO

[75] Inventors: Atsushi Go; Rika Higurashi; Miki Komine; Yoshimi Tsutsumi; Yoshihiro Usui, all of Ibaraki, Japan

[73] Assignee: Rhône-Poulenc Agrochimie, Lyons, France

[21] Appl. No.: 403,433

[22] Filed: Mar. 14, 1995

[30] Foreign Application Priority Data

Oct. 14, 1993 [JP] Japan .................... 5-257218

[51] Int. Cl.[6] .................... A01N 43/72; C07D 413/02
[52] U.S. Cl. .................... 504/223; 544/97; 549/274
[58] Field of Search .................... 544/97; 549/274; 504/223

[56] References Cited

U.S. PATENT DOCUMENTS

| | | | |
|---|---|---|---|
| 5,006,157 | 4/1991 | Ohba et al. | 71/95 |
| 5,436,224 | 7/1995 | Hamatani et al. | 504/233 |

FOREIGN PATENT DOCUMENTS

| | | |
|---|---|---|
| 0372586 | 6/1990 | European Pat. Off. . |
| 0605726 | 7/1994 | European Pat. Off. . |
| 4-89485 | 3/1992 | Japan . |
| 93/15064 | 8/1993 | WIPO . |

OTHER PUBLICATIONS

*Chemical Abstracts*, vol. 117, No. 9, Aug. 31, 1992, abstract No. 90305q.
*Chemical Abstracts*, vol. 119, No. 21, Nov. 22, 1993, abstract No. 219601f.
England, *Journal of Organic Chemistry*, vol. 46, No. 1, Jan. 2, 1981, 147–153.
Maujean et al, *Tetrahedron Letters* No. 33, pp. 2905–2908 (1976).
Sato et al, *Heterocycles*, vol. 17, pp. 297–300 (1982).
Yamamoto et al, *Chem. Pharm. Bull.*, 35(5), 1871–1879 (1987).

*Primary Examiner*—Matthew V. Grumbling
*Attorney, Agent, or Firm*—Burns, Doane, Swecker & Mathis, L.L.P.

[57] ABSTRACT

Novel 1,3-oxazin-4-one derivatives of the formula

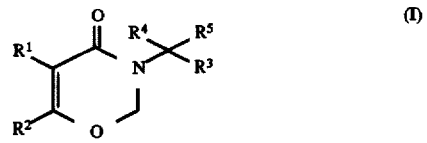

(I)

wherein $R^1$ to $R^5$ are hydrocarbyl radicals which are optionally substituted, and herbicidal compositions comprising the same as active ingredients and their use in controlling the growth of weeds. The compounds can be produced by reacting substituted 1,3-dioxin-4-one derivatives and N-methylene-alkylamine.

51 Claims, No Drawings

HERBICIDAL 1,3-OXAZIN-4-ONE DERIVATIVES AND INTERMEDIATES THERETO

CROSS-REFERENCE TO RELATED APPLICATION

This is a continuation-in-part of International Application No. PCT/EP 94/03310, filed Oct. 6, 1994, designating the United States.

FIELD OF THE INVENTION

This invention relates to novel 1,3-oxazin-4-one derivatives which have not been reported in any previous publication, herbicides containing the same, and process and intermediates for preparing the same.

BACKGROUND ART

Certain types of 4H-2,3-dihydro-1,3-oxazin-4-one derivatives are described in, for example, *Tetrahedron Lett*, (33), 2905 (1976), *Heterocycles*, 17, 298 (1982), *Chem. Pharm. Bull.*, 35(5), 1871(1987).

However, the compounds described in the above publications differ from the compounds of this invention since none of them has a tertiary alkyl or aralkyl substituent on the 3-position, and no mention is made of their herbicidal activity and plant growth regulator activity.

U.S. Pat. No. 5,006,157 discloses 1-(1-methyl-1-phenylethyl)-3-phenyl-1,2,5,6-tetrahydropyridin-2-one derivatives and their use as herbicides. However, 4H-2,3-dihydro-1,3-oxazin-4-one derivatives and their herbicidal activity have not been described at all in the patent description. In addition, it has been found that the compounds disclosed in the patent description are not good enough in herbicidal efficacy and selectivity.

SUMMARY AND OBJECTS OF THE INVENTION

The present inventors have found that a certain type of 1,3-oxazin-4-one derivative shows herbicidal activity at low doses on various weeds without damaging useful crops.

This invention provides 1,3-oxazin-4-one derivatives having the formula:

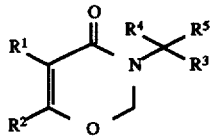

(I)

wherein:

$R^1$ is a lower alkyl radical, a lower alkenyl radical, a lower alkynyl radical, an aryl radical which is unsubstituted or substituted, or an aralkyl radical which is unsubstituted or substituted;

$R^2$ is a lower haloalkyl radical, a lower hydroxyalkyl radical, a lower alkoxyalkyl radical, a lower acyloxyalkyl radical, a formyl radical, a hydroxyiminomethyl radical, a lower alkoxyiminomethyl radical, a lower acyloxyiminomethyl radical, a cyano radical, or a lower alkoxycarbonyl radical;

$R^3$ is a lower alkyl radical, an aryl radical which is unsubstituted or substituted, or an aralkyl radical which is unsubstituted or substituted; and $R^4$ and $R^5$, independently, are each a lower alkyl radical, or $R^4$ and $R^5$, taken together with the carbon atom to which they are bonded, combine to form a 3- to 8-membered carbocyclic ring which may optionally bear one or more alkyl radicals as substituents.

Another object of the present invention is to provide herbicidal compositions comprising one or more compounds of formula (I) as active ingredient.

DETAILED DESCRIPTION OF THE INVENTION AND PREFERRED EMBODIMENTS

Some examples of the groups $R^1$, $R^2$, $R^3$, $R^4$ and $R^5$ as defined in the above formula (I) will be explained as follows:

"Lower alkyl radical" means either a straight-chained or a branched-chained alkyl radical which has 1 to 6 carbon atoms, and includes, for example, methyl, ethyl, n-propyl, isopropyl, n-butyl, isobutyl, sec-butyl, tert-butyl, n-pentyl, neopentyl, tert-pentyl, hexyl, and the like.

"Lower alkenyl radical" means an alkenyl radical which has 2 to 6 carbon atoms, and includes, for example, allyl, 2-methyl-2-propenyl, 2-butenyl, 3-butenyl, 3-methyl-2-butenyl, and the like.

"Lower alkynyl radical" means an alkynyl radical which has 2 to 6 carbon atoms, and includes, for example, 2-propynyl, 1-methyl-2-propynyl, 2-butynyl, 3-butynyl, and the like.

"Lower haloalkyl radical" means a haloalkyl radical which has 1 to 4 carbon atoms, and includes, for example, bromomethyl, dichloromethyl, trifluoromethyl, 1-chloroethyl, 2-iodoethyl, 3-chloropropyl, 2-methyl-2-chloropropyl, 2,2,2-trifluoroethyl, and the like.

"Lower hydroxyalkyl radical" means an hydroxyalkyl radical which has 1 to 4 carbon atoms, and includes, for example, hydroxymethyl, 2-hydroxyethyl, and the like.

"Lower alkoxyalkyl or lower acyloxyiminomethyl radical" means an alkyl radical which has 1 to 4 carbon atoms and is substituted with an alkoxy radical which has 1 to 4 carbon atoms, or with an acyl radical which has 2 to 5 carbon atoms, and includes, for example, methoxymethyl, ethoxymethyl, acetyloxymethyl, and the like.

"Lower alkoxyiminomethyl or lower acyloxyiminomethyl radical" means an iminomethyl radical substituted with an alkoxy radical which has 1 to 4 carbon atoms or with an acyl radical which has 2 to 5 carbon atoms, and includes, for example, methoxyiminomethyl, ethoxyiminomethyl, acetyloxyiminomethyl, and the like.

"Lower alkoxycarbonyl radical" means an alkoxycarbonyl radical which has 2 to 6 carbon atoms, and includes, for example, methoxycarbonyl, ethoxycarbonyl, isopropoxycarbonyl, and the like.

"Aryl radical which is unsubstituted or substituted" means an aryl radical such as phenyl, naphthyl etc. which is optionally substituted with a halogen atom, a lower alkyl radical, a lower alkoxy radical, a lower haloalkyl radical, a lower haloalkoxy radical, a nitro group, etc., and includes, for example, phenyl, 2-naphthyl, 2-fluorophenyl, 2-tolyl, 3-nitrophenyl, 4-chloro-2-naphthyl, 3,5-dichlorophenyl, 3,5-dimethoxyphenyl, 3,5-bis(difluoromethoxy)phenyl, 3,5-dichloro-4-methylphenyl, and the like.

"Aralkyl radical which is unsubstituted or substituted" means an aralkyl radical which has an "aryl radical which is unsubstituted or substituted" as defined above at the position of the aryl radical, and includes, for example, benzyl, (2-chlorophenyl)methyl, 1-(3-chlorophenyl)ethyl, 2-phenylethyl, 1-methyl-1-phenylethyl, 1-methyl-2-phenylethyl, 1-ethyl-2-(3-trifluoromethylphenyl)ethyl, (2-difluoromethoxyphenyl)methyl, 3-phenylpropyl, and the like. The alkyl portion of the aralkyl radical typically has 1 to 4 carbon atoms.

"3 to 8-Membered carbocyclic ring which may optionally bear 1 or more lower alkyl radicals as substituents" includes cyclopropane, cyclobutane, cyclopentane, cyclohexane, cycloheptane, cyclooctane, 2,2'-dimethylcyclopropane, 3,5-diethylcyclohexane, and the like, i.e. cycloalkane rings having 3 to 8 ring atoms, which are unsubstituted or substituted by 1 or more lower alkyl radicals.

Further, examples of a halogen atom, a lower alkoxy radical, a lower haloalkyl radical, a lower haloalkoxy radial, and a lower acyl radical will be explained as follows:

"Halogen atom" mean fluorine, chlorine, bromine or iodine.

"Lower alkoxy radical" means an alkoxy radical which has a lower alkyl radical as defined above at the position of the alkyl radical, and includes, for example, methoxy, ethoxy, propoxy, isopropoxy, butoxy, pentoxy, and the like.

"Lower haloalkyl radical" means a lower alkyl radical of which one or more hydrogen atoms are replaced with (a) halogen atom(s) as defined above, and includes, for example, bromomethyl, dichloromethyl, trifluoromethyl, 1-chloroethyl, 2-iodoethyl, 3-chloropropyl, 2-methyl-2-chloropropyl, 2,2,2-trifluoroethyl, and the like.

"Lower haloalkoxy radical" means a haloalkoxy radical which has a lower haloalkyl radical as defined above at the position of alkyl radical, and includes, for example, trifluoromethoxy, difluoromethoxy, chlorodifluoromethoxy, 2-chloroethoxy, 1,1,2,2-tetrafluoroethoxy, 3-chloropropoxy, 2,2,3,3,3-pentafluoropropoxy, and the like.

"Lower acyl radical" means an acyl radical having up to 6 carbon atoms in the alkyl portion, such as acetyl, propionyl, butyryl, isobutyryl, and the like.

Any groups which have not been described above can be selected from already described atoms or groups by optional combination or in the well-known usual way.

Among the compounds of this invention having formula (I) defined above, some preferable compounds are selected as follows:

$R^1$ is a branched alkyl radical such as isobutyl or isopropyl; or a phenyl radical, without substitution or substituted with a halogen atom or a lower alkyl radical;

$R^3$ is phenyl or 2-naphthyl, without substitution or substituted with one or two halogen atom(s), a lower haloalkyl radical or a lower haloalkoxy radical;

$R^4$ and $R^5$, independently, are each methyl.

More preferably, the compounds are selected from those of the formula:

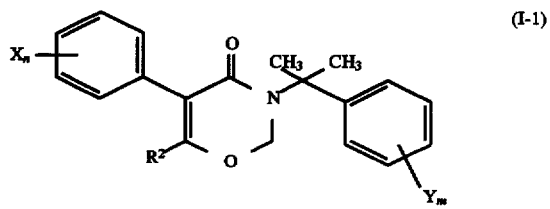

(I-1)

wherein $R^2$ is as defined with formula (I) above; X is a halogen atom or a lower alkyl radical; Y is a halogen atom or a lower haloalkyl radical; n is 0 or 1; and m is 0, 1 or 2.

According to the studies of the present inventors, the compounds having the formula (II-2) below, which can be intermediates to the compounds of this invention wherein $R^1$ is an aryl radical which may be substituted and $R^2$ is an acetyloxymethyl radical, i.e. the compounds of the formula:

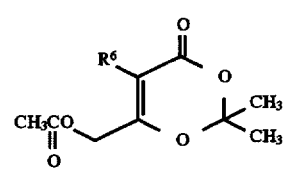

(II-2)

wherein $R^6$ is an aryl radical which may be substituted; and the compounds having the formula (II-1) below, which can be derived from the compounds of formula (II-2) above, i.e. the compounds of the formula:

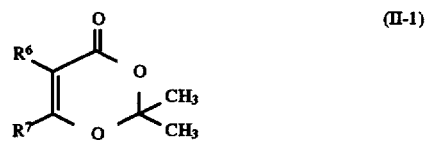

(II-1)

wherein $R^6$ is an aryl radical which may be substituted and $R^7$ is a hydroxymethyl or a formyl radical, are novel compounds, and therefore are included in this invention.

Thus, this invention can provide 1,3-dioxin-4-one derivatives having the formula:

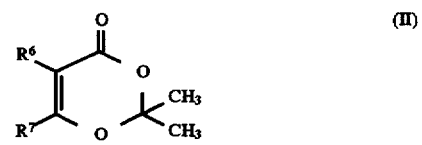

(II)

wherein $R^6$ is an aryl radical which may be substituted and $R^7$ is a hydroxymethyl, an acetyloxymethyl or a formyl radical.

In formula (II) above:

"$R^6$ is an aryl radical which may be substituted" means an aryl radical such as phenyl or naphthyl, or such an aryl radical which is substituted with a halogen atom, a lower alkyl radical, a lower alkoxy radical, a lower haloalkyl radical, a nitro group, etc. From these substitutions, a phenyl radical substituted at the 2-position can be selected preferably.

In formula (II) above, examples of groups defined by $R^6$ are exactly the same as described previously.

Examples of specific compounds of this invention having formula (I) are shown in Table 1 below, and those having formula (II) are shown in Table 2 below.

(A)

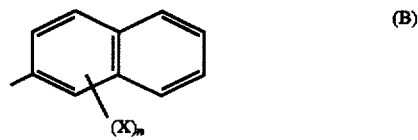

(B)

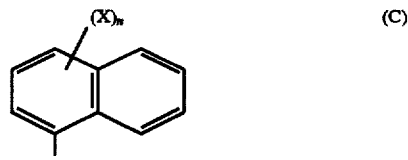

(C)

-continued

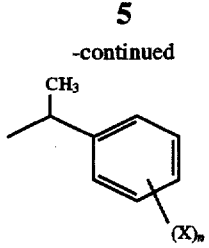 (E)

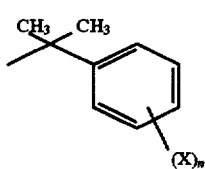 (F)

(a)

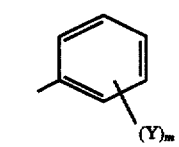

(b)

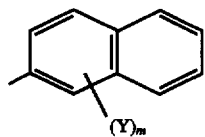

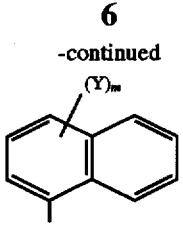 (c)

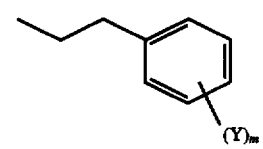 (d)

The abbreviations in the Tables are as follows.

Me = Methyl radical;     Et = Ethyl radical;
Pr = Propyl radical;     iPr = Propyl radical;
Bu = Butyl radical;      tBu - tert-Butyl radical;
Ac = Acetyl radical;     — = no substitution

TABLE 1

| Compd. No. | R$^1$ (X)$_n$ | | R$^2$ | R$^3$ (Y)$_m$ | | R$^4$ | R$^5$ |
|---|---|---|---|---|---|---|---|
| 1  | (A) | —     | CH$_2$F | (a) | —         | Me | Me |
| 2  | (A) | —     | CH$_2$F | (a) | 3-F       | Me | Me |
| 3  | (A) | —     | CH$_2$F | (a) | 3-Cl      | Me | Me |
| 4  | (A) | —     | CH$_2$F | (a) | 3-Cl, 5-Cl| Me | Me |
| 5  | (A) | —     | CH$_2$F | (a) | 3-Me      | Me | Me |
| 6  | (A) | —     | CH$_2$F | (a) | 3-CF$_3$  | Me | Me |
| 7  | (A) | 2-F   | CH$_2$F | (a) | —         | Me | Me |
| 8  | (A) | 2-F   | CH$_2$F | (a) | 3-Cl, 5-Cl| Me | Me |
| 9  | (A) | 2-Cl  | CH$_2$F | (a) | —         | Me | Me |
| 10 | (A) | 2-Cl  | CH$_2$F | (a) | 3-Cl, 5-Cl| Me | Me |
| 11 | (A) | 2-Me  | CH$_2$F | (a) | —         | Me | Me |
| 12 | (A) | 3-Me  | CH$_2$F | (a) | —         | Me | Me |
| 13 | (A) | 2-CF$_3$ | CH$_2$F | (a) | —      | Me | Me |
| 14 | (A) | —     | CH$_2$F | (b) | —         | Me | Me |
| 15 | (A) | —     | CH$_2$F | (b) | 4-Cl      | Me | Me |
| 16 | (A) | —     | CH$_2$F | (c) | —         | Me | Me |
| 17 | (B) | —     | CH$_2$F | (a) | —         | Me | Me |
| 18 | (B) | —     | CH$_2$F | (a) | 3-Cl      | Me | Me |
| 19 | (B) | —     | CH$_2$F | (a) | 3-Cl, 5-Cl| Me | Me |
| 20 | (C) | —     | CH$_2$F | (a) | —         | Me | Me |
| 21 | (C) | —     | CH$_2$F | (a) | 3-Cl      | Me | Me |
| 22 | (A) | —     | CH$_2$F |     | Me        | Me | Me |
| 23 | (A) | —     | CH$_2$F |     | Et        | Me | Me |
| 24 | (A) | —     | CH$_2$F |     | Pr        | Me | Me |
| 25 | (A) | —     | CH$_2$F |     | tBu       | Me | Me |
| 26 |     | Me    | CH$_2$F | (a) | —         | Me | Me |
| 27 |     | Me    | CH$_2$F | (a) | 3-Cl, 5-Cl| Me | Me |
| 28 |     | Et    | CH$_2$F | (a) | —         | Me | Me |
| 29 |     | Et    | CH$_2$F | (a) | 3-Cl, 5-Cl| Me | Me |

TABLE 1-continued

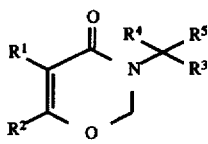

| Compd. No. | R¹ (X)ₙ | | R² | R³ (Y)ₘ | | R⁴ | R⁵ |
|---|---|---|---|---|---|---|---|
| 30 | | iPr | CH₂F | (a) | — | Me | Me |
| 31 | | iPr | CH₂F | (a) | 3-Cl, 5-Cl | Me | Me |
| 32 | | Bu | CH₂F | (a) | — | Me | Me |
| 33 | | Bu | CH₂F | (a) | 3-Cl, 5-Cl | Me | Me |
| 34 | (A) | — | CHF₂ | (a) | — | Me | Me |
| 35 | (A) | — | CHF₂ | (a) | 3-Cl | Me | Me |
| 36 | (A) | — | CHF₂ | (a) | 3-Cl, 5-Cl | Me | Me |
| 37 | (A) | 2-F | CHF₂ | (a) | — | Me | Me |
| 38 | (A) | 2-Cl | CHF₂ | (a) | — | Me | Me |
| 39 | (A) | 2-Me | CHF₂ | (a) | — | Me | Me |
| 40 | (A) | — | CHF₂ | (b) | — | Me | Me |
| 41 | (A) | — | CHF₂ | (c) | — | Me | Me |
| 42 | (B) | — | CHF₂ | (a) | — | Me | Me |
| 43 | (C) | — | CHF₂ | (a) | — | Me | Me |
| 44 | (A) | — | CHF₂ | | Me | Me | Me |
| 45 | (A) | — | CHF₂ | | Et | Me | Me |
| 46 | | Me | CHF₂ | (a) | — | Me | Me |
| 47 | | Me | CHF₂ | (a) | 3-Cl, 5-Cl | Me | Me |
| 48 | (A) | — | CF₃ | (a) | — | Me | Me |
| 49 | (A) | — | CF₃ | (a) | 3-Cl, 5-Cl | Me | Me |
| 50 | (A) | — | CF₃ | (b) | — | Me | Me |
| 51 | (A) | — | CF₃ | (c) | — | Me | Me |
| 52 | (A) | — | CF₃ | | Me | Me | Me |
| 53 | (A) | — | CH₂OH | (a) | — | Me | Me |
| 54 | (A) | — | CH₂OH | (a) | 3-Cl | Me | Me |
| 55 | (A) | — | CH₂OH | (a) | 3-Cl, 5-Cl | Me | Me |
| 56 | (A) | — | CH₂OH | (b) | — | Me | Me |
| 57 | (A) | — | CH₂OH | (c) | — | Me | Me |
| 58 | (B) | — | CH₂OH | (a) | — | Me | Me |
| 59 | (C) | — | CH₂OH | (a) | — | Me | Me |
| 60 | (A) | — | CH₂OH | | Me | Me | Me |
| 61 | (A) | — | CH₂OH | | Et | Me | Me |
| 62 | | Me | CH₂OH | (a) | — | Me | Me |
| 63 | | Et | CH₂OH | (a) | — | Me | Me |
| 64 | | iPr | CH₂OH | (a) | — | Me | Me |
| 65 | | Bu | CH₂OH | (a) | — | Me | Me |
| 66 | (A) | — | CH₂OAc | (a) | — | Me | Me |
| 67 | (A) | — | CH₂OAc | (a) | 3-F | Me | Me |
| 68 | (A) | — | CH₂OAc | (a) | 3-Cl | Me | Me |
| 69 | (A) | — | CH₂OAc | (a) | 3-Cl, 5-Cl | Me | Me |
| 70 | (A) | — | CH₂OAc | (a) | 3-Me | Me | Me |
| 71 | (A) | — | CH₂OAc | (a) | 3-CF₃ | Me | Me |
| 72 | (A) | — | CH₂OAc | (a) | 3-OMe | Me | Me |
| 73 | (A) | 2-F | CH₂OAc | (a) | — | Me | Me |
| 74 | (A) | 2-F | CH₂OAc | (a) | 3-Cl, 5-Cl | Me | Me |
| 75 | (A) | 2-Cl | CH₂OAc | (a) | — | Me | Me |
| 76 | (A) | 2-Cl | CH₂OAc | (a) | 3-Cl, 5-Cl | Me | Me |
| 77 | (A) | 3-Cl | CH₂OAc | (a) | — | Me | Me |
| 78 | (A) | 3-Cl | CH₂OAc | (a) | 3-Cl, 5-Cl | Me | Me |
| 79 | (A) | 2-Me | CH₂OAc | (a) | — | Me | Me |
| 80 | (A) | 2-Me | CH₂OAc | (a) | 3-Cl, 5-Cl | Me | Me |
| 81 | (A) | 3-Me | CH₂OAc | (a) | — | Me | Me |
| 82 | (A) | 3-Me | CH₂OAc | (a) | 3-Cl, 5-Cl | Me | Me |
| 83 | (A) | — | CH₂OAc | (b) | — | Me | Me |
| 84 | (A) | — | CH₂OAc | (b) | 4-Cl | Me | Me |
| 85 | (A) | — | CH₂OAc | (c) | — | Me | Me |
| 86 | (A) | — | CH₂OAc | (c) | 3-Cl | Me | Me |
| 87 | (A) | — | CH₂OAc | (d) | — | Me | Me |
| 88 | (A) | — | CH₂OAc | (d) | 2-Cl | Me | Me |
| 89 | (A) | — | CH₂OAc | (d) | 2-Me | Me | Me |
| 90 | (B) | — | CH₂OAc | (a) | — | Me | Me |
| 91 | (B) | — | CH₂OAc | (a) | 3-Cl, 5-Cl | Me | Me |
| 92 | (C) | — | CH₂OAc | (a) | — | Me | Me |
| 93 | (C) | — | CH₂OAc | (a) | 3-Cl, 5-Cl | Me | Me |
| 94 | (E) | — | CH₂OAc | (a) | — | Me | Me |
| 95 | (E) | — | CH₂OAc | (a) | 3-Cl, 5-Cl | Me | Me |
| 96 | (F) | — | CH₂OAc | (a) | — | Me | Me |
| 97 | (F) | — | CH₂OAc | (a) | 3-Cl, 5-Cl | Me | Me |

TABLE 1-continued

| Compd. No. | R¹ (X)ₙ | | R² | R³ (Y)ₘ | | R⁴ | R⁵ |
|---|---|---|---|---|---|---|---|
| 98 | (A) | — | CH₂OAc | | Me | Me | Me |
| 99 | (A) | — | CH₂OAc | | Et | Me | Me |
| 100 | (A) | — | CH₂OAc | | Pr | Me | Me |
| 101 | (A) | — | CH₂OAc | | iPr | Me | Me |
| 102 | (A) | — | CH₂OAc | | Bu | Me | Me |
| 103 | (A) | — | CH₂OAc | | tBu | Me | Me |
| 104 | Me | | CH₂OAc | (a) | — | Me | Me |
| 105 | Me | | CH₂OAc | (a) | 3-Cl, 5-Cl | Me | Me |
| 106 | Et | | CH₂OAc | (a) | — | Me | Me |
| 107 | Et | | CH₂OAc | (a) | 3-Cl, 5-Cl | Me | Me |
| 108 | CH=CH₂ | | CH₂OAc | (a) | — | Me | Me |
| 109 | CH=CH₂ | | CH₂OAc | (a) | 3-Cl, 5-Cl | Me | Me |
| 110 | CH₂CH=CH₂ | | CH₂OAc | (a) | — | Me | Me |
| 111 | CH₂CH=CH₂ | | CH₂OAc | (a) | 3-Cl, 5-Cl | Me | Me |
| 112 | C≡CH | | CH₂OAc | (a) | — | Me | Me |
| 113 | C≡CH | | CH₂OAc | (a) | 3-Cl, 5-Cl | Me | Me |
| 114 | (A) | — | CH₂OAc | (a) | — | Me | Me |
| 115 | (A) | — | CH₂OAc | (a) | 3-Cl | Me | Me |
| 116 | (A) | — | CH₂OAc | (a) | 3-Cl, 5-Cl | Me | Me |
| 117 | (A) | — | CH₂OAc | (b) | — | Me | Me |
| 118 | (A) | — | CH₂OAc | (c) | — | Me | Me |
| 119 | (A) | — | CH₂OAc | | Me | Me | Me |
| 120 | (A) | — | CH₂OAc | | Et | Me | Me |
| 121 | (A) | — | CHO | (a) | — | Me | Me |
| 122 | (A) | — | CHO | (a) | 3-Cl, 5-Cl | Me | Me |
| 123 | (A) | — | CHO | (b) | — | Me | Me |
| 124 | (A) | — | CHO | (c) | — | Me | Me |
| 125 | (A) | — | CHO | (d) | — | Me | Me |
| 126 | (B) | — | CHO | (a) | — | Me | Me |
| 127 | (B) | — | CHO | (a) | 3-Cl, 5-Cl | Me | Me |
| 128 | (C) | — | CHO | (a) | — | Me | Me |
| 129 | (A) | — | CHO | | Me | Me | Me |
| 130 | (A) | — | CHO | | Et | Me | Me |
| 131 | (A) | — | CHO | | Pr | Me | Me |
| 132 | Me | | CHO | (a) | — | Me | Me |
| 133 | Et | | CHO | (a) | — | Me | Me |
| 134 | (A) | — | CH=NOH | (a) | — | Me | Me |
| 135 | (A) | — | CH=NOH | (a) | 3-Cl, 5-Cl | Me | Me |
| 136 | (A) | — | CH=NOH | (b) | — | Me | Me |
| 137 | (A) | — | CH=NOH | (c) | — | Me | Me |
| 138 | (B) | — | CH=NOH | (a) | — | Me | Me |
| 139 | (C) | — | CH=NOH | (a) | — | Me | Me |
| 140 | (A) | — | CH=NOH | | Me | Me | Me |
| 141 | (A) | — | CH=NOH | | Et | Me | Me |
| 142 | (A) | — | CH=NOH | | Pr | Me | Me |
| 143 | (A) | — | CH=NOH | | iPr | Me | Me |
| 144 | Me | | CH=NOH | (a) | — | Me | Me |
| 145 | (A) | — | CH=NOAc | (a) | — | Me | Me |
| 146 | (A) | — | CH=NOAc | (a) | 3-Cl | Me | Me |
| 147 | (A) | — | CH=NOAc | (a) | 3-Cl, 5-Cl | Me | Me |
| 148 | (A) | 2-F | CH=NOAc | (a) | — | Me | Me |
| 149 | (A) | 2-F | CH=NOAc | (a) | 3-Cl, 5-Cl | Me | Me |
| 150 | (A) | 2-Cl | CH=NOAc | (a) | — | Me | Me |
| 151 | (A) | 2-Cl | CH=NOAc | (a) | 3-Cl, 5-Cl | Me | Me |
| 152 | (A) | 2-Me | CH=NOAc | (a) | — | Me | Me |
| 153 | (A) | 2-Me | CH=NOAc | (a) | 3-Cl, 5-Cl | Me | Me |
| 154 | (A) | — | CH=NOAc | (b) | — | Me | Me |
| 155 | (A) | — | CH=NOAc | (c) | — | Me | Me |
| 156 | (A) | — | CH=NOAc | | Me | Me | Me |
| 157 | (A) | — | CH=NOAc | | Et | Me | Me |
| 158 | (A) | — | CH=NOMe | (a) | — | Me | Me |
| 159 | (A) | — | CH=NOMe | (a) | 3-Cl | Me | Me |
| 160 | (A) | — | CH=NOMe | (a) | 3-Cl, 5-Cl | Me | Me |
| 161 | (A) | — | CH=NOMe | (b) | — | Me | Me |
| 162 | (A) | — | CH=NOMe | | Me | Me | Me |
| 163 | (A) | — | CH=NOMe | | Et | Me | Me |

TABLE 1-continued

| Compd. No. | R$^1$ (X)$_n$ | R$^2$ | R$^3$ (Y)$_m$ | | R$^4$ | R$^5$ |
|---|---|---|---|---|---|---|
| 164 | (A) — | CN | (a) | — | Me | Me |
| 165 | (A) — | CN | (a) | 3-F | Me | Me |
| 166 | (A) — | CN | (a) | 3-Cl | Me | Me |
| 167 | (A) — | CN | (a) | 3-Cl, 5-Cl | Me | Me |
| 168 | (A) — | CN | (a) | 3-Me | Me | Me |
| 169 | (A) — | CN | (a) | 3-CF$_3$ | Me | Me |
| 170 | (A) — | CN | (b) | — | Me | Me |
| 171 | (A) — | CN | (c) | — | Me | Me |
| 172 | (B) — | CN | (a) | — | Me | Me |
| 173 | (B) — | CN | (a) | 3-Cl, 5-Cl | Me | Me |
| 174 | (A) — | CN | | Me | Me | Me |
| 175 | (A) — | CN | | Et | Me | Me |
| 176 | (A) — | COOMe | (a) | — | Me | Me |
| 177 | (A) — | COOMe | (a) | 3-Cl, 5-Cl | Me | Me |
| 178 | (A) — | COOMe | (b) | — | Me | Me |
| 179 | (A) — | COOMe | | Me | Me | Me |
| 180 | (A) — | COOMe | | Et | Me | Me |
| 181 | (A) — | COOEt | (a) | — | Me | Me |
| 182 | (A) — | COOEt | (a) | 3-Cl, 5-Cl | Me | Me |
| 183 | (A) — | COOEt | (b) | — | Me | Me |
| 184 | (A) — | COOEt | | Me | Me | Me |
| 185 | (A) — | COOEt | | Et | Me | Me |
| 186 | (A) — | CH$_2$F | (a) | — | Me | Et |
| 187 | (A) — | CHF$_2$ | (a) | — | Me | Et |
| 188 | (A) — | CF$_3$ | (a) | — | Me | Et |
| 189 | (A) — | CH$_2$OH | (a) | — | Me | Et |
| 190 | (A) — | CH$_2$OH | (a) | 3-Cl | Me | Et |
| 191 | (A) — | CH$_2$OH | (a) | 3-Cl, 5-Cl | Me | Et |
| 192 | (A) — | CH$_2$OAc | (a) | — | Me | Et |
| 193 | (A) — | CH$_2$OMe | (a) | — | Me | Et |
| 194 | (A) — | CHO | (a) | — | Me | Et |
| 195 | (A) — | CHO | (a) | 3-Cl | Me | Et |
| 196 | (A) — | CHO | (a) | 3-Cl, 5-Cl | Me | Et |
| 197 | (A) — | CH=NOH | (a) | — | Me | Et |
| 198 | (A) — | CH=NOAc | (a) | — | Me | Et |
| 199 | (A) — | CH=NOMe | (a) | — | Me | Et |
| 200 | (A) — | CN | (a) | — | Me | Et |
| 201 | (A) — | COOMe | (a) | — | Me | Et |
| 202 | (A) — | CH$_2$F | (a) | — | —CH$_2$CH$_2$— | |
| 203 | (A) — | CHF$_2$ | (a) | — | —CH$_2$CH$_2$— | |
| 204 | (A) — | CF$_3$ | (a) | — | —CH$_2$CH$_2$— | |
| 205 | (A) — | CH$_2$OH | (a) | — | —CH$_2$CH$_2$— | |
| 206 | (A) — | CH$_2$OAc | (a) | — | —CH$_2$CH$_2$— | |
| 207 | (A) — | CHO | (a) | — | —CH$_2$CH$_2$— | |
| 208 | (A) — | CN | (a) | — | —CH$_2$CH$_2$— | |
| 209 | (A) — | CH$_2$F | (a) | — | —CH$_2$CH$_2$CH$_2$— | |
| 210 | (A) — | CHF$_2$ | (a) | — | —CH$_2$CH$_2$CH$_2$— | |
| 211 | (A) — | CF$_3$ | (a) | — | —CH$_2$CH$_2$CH$_2$— | |
| 212 | (A) — | CH$_2$OH | (a) | — | —CH$_2$CH$_2$CH$_2$— | |
| 213 | (A) — | CH$_2$OAc | (a) | — | —CH$_2$CH$_2$CH$_2$— | |
| 214 | (A) — | CHO | (a) | — | —CH$_2$CH$_2$CH$_2$— | |
| 215 | (A) — | CN | (a) | — | —CH$_2$CH$_2$CH$_2$— | |
| 216 | (A) — | CH$_2$F | (a) | — | —CH$_2$(CH$_2$)$_2$CH$_2$— | |
| 217 | (A) — | CHF$_2$ | (a) | — | —CH$_2$(CH$_2$)$_2$CH$_2$— | |
| 218 | (A) — | CF$_3$ | (a) | — | —CH$_2$(CH$_2$)$_2$CH$_2$— | |
| 219 | (A) — | CH$_2$OH | (a) | — | —CH$_2$(CH$_2$)$_2$CH$_2$— | |
| 220 | (A) — | CH$_2$OH | (a) | 3-Cl | —CH$_2$(CH$_2$)$_2$CH$_2$— | |
| 221 | (A) — | CH$_2$OAc | (a) | — | —CH$_2$(CH$_2$)$_2$CH$_2$— | |
| 222 | (A) — | CH$_2$OAc | (a) | 3-Cl | —CH$_2$(CH$_2$)$_2$CH$_2$— | |
| 223 | (A) — | CHO | (a) | — | —CH$_2$(CH$_2$)$_2$CH$_2$— | |
| 224 | (A) — | CHO | (a) | 3-Cl | —CH$_2$(CH$_2$)$_2$CH$_2$— | |
| 225 | (A) — | CN | (a) | — | —CH$_2$(CH$_2$)$_2$CH$_2$— | |
| 226 | (A) — | CH$_2$F | (a) | — | —CH$_2$(CH$_2$)$_3$CH$_2$— | |
| 227 | (A) — | CHF$_2$ | (a) | — | —CH$_2$(CH$_2$)$_3$CH$_2$— | |
| 228 | (A) — | CF$_3$ | (a) | — | —CH$_2$(CH$_2$)$_3$CH$_2$— | |
| 229 | (A) — | CH$_2$OH | (a) | — | —CH$_2$(CH$_2$)$_3$CH$_2$— | |
| 230 | (A) — | CH$_2$OH | (a) | 3-Cl | —CH$_2$(CH$_2$)$_3$CH$_2$— | |
| 231 | (A) — | CH$_2$OAc | (a) | — | —CH$_2$(CH$_2$)$_3$CH$_2$— | |

TABLE 1-continued

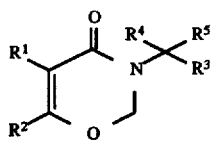

| Compd. No. | R¹ (X)ₙ | R² | R³ (Y)ₘ | R⁴ | R⁵ |
|---|---|---|---|---|---|
| 232 | (A) — | CH₂OAc | (a) 3-Cl | —CH₂(CH₂)₃CH₂— | |
| 233 | (A) — | CHO | (a) — | —CH₂(CH₂)₃CH₂— | |
| 234 | (A) — | CHO | (a) 3-Cl | —CH₂(CH₂)₃CH₂— | |
| 235 | (A) — | CN | (a) — | —CH₂(CH₂)₃CH₂— | |

TABLE 2

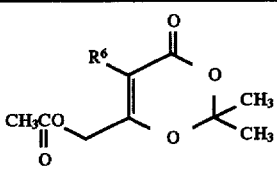

| Compd. No. | R⁶ | (X)ₙ | R⁷ |
|---|---|---|---|
| 236 | (A) | — | CH₂OH |
| 237 | (A) | 2-F | CH₂OH |
| 238 | (A) | 2-Cl | CH₂OH |
| 239 | (A) | 2-Me | CH₂OH |
| 240 | (B) | — | CH₂OH |
| 241 | (A) | — | CH₂OAc |
| 242 | (A) | 2-F | CH₂OAc |
| 243 | (A) | 2-Cl | CH₂OAc |
| 244 | (A) | 2-Me | CH₂OAc |
| 245 | (B) | — | CH₂OAc |
| 246 | (A) | — | CHO |
| 247 | (A) | 2-F | CHO |

The compounds of the present invention having formula (I) can be prepared, for example, by the following process; however, this invention is not limited by this example.

Method A:

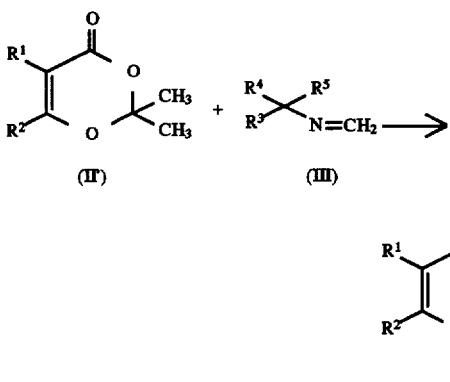

The compounds of formula (I) of this invention can thus be prepared by reacting the compounds of formula (II') with the compounds of formula (III) in a suitable solvent or without solvent.

The reaction temperature can be set optionally between 90° and 160° C., or in the range of the boiling point of the solvent used.

Insofar as concerns the solvent, there is no limitation thereon; any solvent may be used which is substantially inert. However, it is preferred from the viewpoint of the reaction temperature to use solvents with high boiling points such as toluene, xylene, mesitylene and the like.

Reaction time may vary depending upon the reaction conditions used; typically, the reaction may be completed in 1 to 120 minutes.

Further, there is no strict limitation for the proportions of the compounds of formula (III) to the compounds of formula (II'); however, it is convenient to use the compounds of formula (III) in an amount within the range of usually 0.5 to 2 moles, and particularly 0.9 to 1.1 moles, per mole of the compounds of formula (II').

Separation and purification of the compounds of formula (I) produced in this manner may be carried out by methods known per se, such as recrystallization and column chromatography.

The compounds of formula (II') which are used as starting materials in the above chemical reaction can be prepared by the same production methods as the compounds of formula (II) of this invention. The production methods for the compounds of formula (II) will be described later in detail.

The compounds of formula (III) which are used as starting materials for the above chemical reaction can be prepared by methods known per se, for example, the methods described in U.S. Pat. No. 2,582,128, or related methods.

It has been found that the compounds of formula (III) are mostly in equilibrium states with trimers represented by the formula below at around room temperature, and sometimes exist as mixtures therewith, or can exist in some cases as trimers alone, although this differs somewhat according to different substitutions. The equilibrium can be represented:

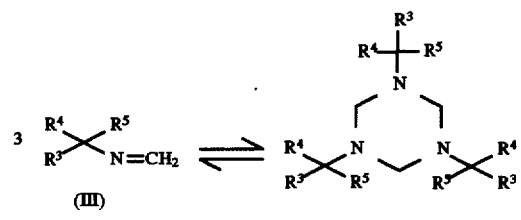

wherein $R^3$, $R^4$ and $R^5$ are as defined with formula (I) hereinabove.

Therefore, although the compounds of formula (III) include not only monomers but also mixtures of the above-described trimers and the monomers, they are represented herein by the structures and names of the monomers for the sake of simplicity.

Method B:

As substitutes for the compounds of formula (II') in the above process, the compounds of the formula:

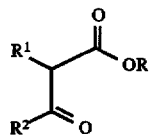

wherein $R^1$ and $R^2$ are as defined above with formula (I) and R is a lower alkyl radical, can be used.

More specifically, the compounds of formula (I) of this invention can be prepared by the following process:

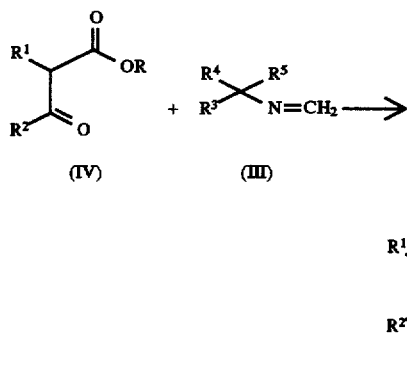

wherein $R^1$, $R^2$, $R^3$, $R^4$ and $R^5$ are as defined with formula (I) described previously; and R is a lower alkyl radical.

The compounds of formula (I) of this invention can thus be prepared by reacting the compounds of formula (IV) with the compounds of formula (III) in a suitable solvent or without solvent. The details of this reaction are exactly the same as the production of the compounds of formula (I) by Method A, except that the compounds of formula (II') in Method A are replaced with the compounds of formula (IV).

The compounds of formula (IV) can be prepared by methods known per se or methods related to those.

Method C:

In addition, there is another method for preparing the compounds of formula (I) of this invention. An acetyloxymethyl radical of the compounds of this invention having formula (I-2) is converted step by step as seen in the Method C herebelow:

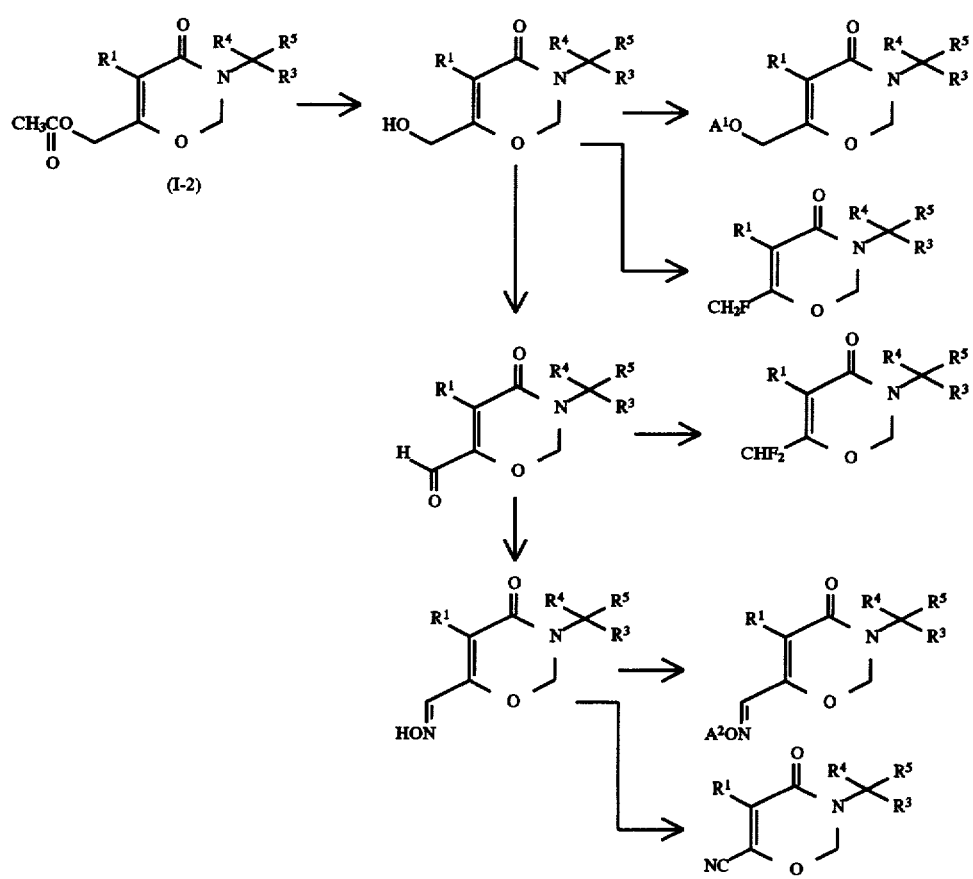

wherein $R^1$, $R^3$, $R^4$ and $R^5$ are as defined with formula (I) hereinabove, $A^1$ is a lower alkyl radical and $A^2$ is a lower alkyl or lower acyl radical, by procedures such as are illustrated in the synthetic Example set forth below.

The compounds of formula (I-2) can be prepared, for example, by Method A from the compounds of formula (II-2) of this invention described hereinabove.

Next, the production methods for the compounds of formula (II) will be explained. However, this invention is not limited by these production methods.

Among the compounds of formula (II), the compounds of formula (II-2) can be prepared, for example, by the following process:

$$\underset{(V)}{\overset{R^6}{\underset{CH_3}{\Large\diagdown}}\ \ \overset{O}{\overset{\|}{C}}\ \ \overset{O}{\underset{O}{\diagdown}}\ \ \overset{CH_3}{\underset{CH_3}{\diagup\!\!\!\diagdown}}} \xrightarrow{\text{halogenation reagent}}$$

$$\underset{(VI)}{\overset{R^6}{\underset{Z}{\diagdown}}\ \ \overset{O}{\overset{\|}{C}}\ \ \overset{O}{\underset{O}{\diagdown}}\ \ \overset{CH_3}{\underset{CH_3}{\diagup\!\!\!\diagdown}}} \xrightarrow{CH_3CO_2M}$$

$$\underset{(II-2)}{\overset{R^6}{\underset{CH_3CO\underset{\|}{O}O}{\diagdown}}\ \ \overset{O}{\overset{\|}{C}}\ \ \overset{O}{\underset{O}{\diagdown}}\ \ \overset{CH_3}{\underset{CH_3}{\diagup\!\!\!\diagdown}}}$$

wherein $R^6$ is an aryl radical which may be substituted, Z is a halogen atom and M is an alkali metal.

The compounds of formula (VI) can be prepared by reacting the compounds of formula (V) with a halogenation reagent in a suitable solvent or without solvent. The reaction temperature can be set optionally in the range from ice cooling temperature to the boiling point of the solvent used.

Although the reaction time may vary depending upon the other reaction conditions, usually the reaction can be completed in 1 to 24 hours.

As the halogenation reagent, for example, chlorine, bromine, N-chlorosuccinimide, or N-bromosuccinimide can be used.

As solvent in case of reaction in a solvent, there is no limitation thereon; any solvent may be used which is substantially inert. For example, carbon tetrachloride, chloroform or acetic acid can be used.

There is no strict limitation for the proportions of the halogenation reagent to the compounds of formula (V); however, it is convenient to use the halogenation reagent in an amount within 0.5 to 2 moles per mole of the compounds of formula (V).

It is also possible to accelerate the chemical reaction by adding catalysts or by lighting.

The product of formula (VI) can be isolated from the reaction mixture and can be purified by methods known per se, such as recrystallization and column chromatography.

Then, the compounds of formula (II-2) of this invention can be prepared by reacting the compounds of formula (VI) produced above with an alkali metal salt of acetic acid, such as sodium acetate, in a suitable solvent. The reaction temperature can be set optionally in the range from room temperature to the boiling point of the solvent used.

Although the reaction time may vary depending on the other reaction conditions, usually the reaction can be completed in 1 to 12 hours.

As solvent, there is no limitation so long as it is substantially inert during the chemical reaction described above.

Further, there is no strict limitation for the proportion of alkali metal salt of acetic acid to the compounds of formula (VI), and it is convenient to use the alkali metal salt of acetic acid in an amount within the range of 0.5 to 5 moles per mole of the compounds of formula (VI).

The products of formula (II-2) can be isolated from the reaction mixture by methods known per se, and can be purified by recrystallization and column chromatography.

The compounds of formula (V) used as starting materials can be prepared by already known methods, for example as published in Chem. Pharm. Bull., 31 (6), 1895 (1983).

Among the compounds of formula (II) described hereinabove, the compounds of formula (II-1) above can be prepared by converting, step by step, the acetyloxymethyl group of the compounds of formula (II-2) to the hydroxymethyl group and then to the formyl group by already known methods, i.e. according to the scheme:

$$\underset{(II-2)}{\overset{R^6}{\underset{CH_3CO\underset{\|}{O}O}{\diagdown}}\ \ \overset{O}{\overset{\|}{C}}\ \ \overset{O}{\underset{O}{\diagdown}}\ \ \diagup\!\!\!\diagdown} \longrightarrow$$

$$\underset{(II-1-a)}{\overset{R^6}{\underset{HO}{\diagdown}}\ \ \overset{O}{\overset{\|}{C}}\ \ \overset{O}{\underset{O}{\diagdown}}\ \ \diagup\!\!\!\diagdown} \longrightarrow \underset{(II-1-b)}{\overset{R^6}{\underset{H\underset{\|}{O}}{\diagdown}}\ \ \overset{O}{\overset{\|}{C}}\ \ \overset{O}{\underset{O}{\diagdown}}\ \ \overset{CH_3}{\underset{CH_3}{\diagup\!\!\!\diagdown}}}$$

wherein $R^6$ is an aryl radical which may be substituted.

The compounds of formula (II-1-a) can be prepared from the compounds of formula (II-2) by reacting in a suitable solvent or without solvent, for example, hydrolysis in the presence of base or ester-exchange with a lower alcohol.

Further, the compounds of formula (II-1-b) can be prepared from the compounds of formula (II-1-a), for example, by reacting with an oxidizing reagent in a suitable solvent and with a catalyst, if needed.

As oxidizing reagent, for example, chromium oxide, chromate, dichromate, manganese dioxide, oxygen or dimethylsulfoxide can be used.

The novel compounds of formula (I) of the present invention have herbicidal activity; therefore, new herbicidal compositions comprising the compounds of formula (I) as active ingredients are also provided by the present invention.

When the compounds of this invention are used as herbicides, they are mixed with carriers or diluents, as well as, when desired, various additives and auxiliaries, by methods known per se and formed into a formulate which is acceptable for use as agricultural compositions, for instance, dusts, granules, wettable powders, emulsifiable concentrates, soluble powders, flowable compositions, etc. They can be used as mixtures or in combination with other agricultural chemicals, for example, fungicides, insecticides, acaricides, herbicides, plant growth regulators, fertilizers, and/or soil conditioners.

In particular, the use of the compounds of this invention as mixtures with other herbicides can lead not only to reduction in dose, and/or reduction in manpower, but also to broadening of the herbicidal spectrum attributable to cooperative activities and further improved effects attributable to synergistic activities by both agents.

The carriers or diluents used for formulation herein include generally solid or liquid carriers or diluents.

Examples of appropriate solid carriers or diluents include clays represented by kaolinites, montmorillonites, illites, polygroskites, etc., more specifically pyrophyllite, attapulgite, sepiolite, kaolinite, bentonite, vermiculite, mica, talc, etc.; and other inorganic substances such as gypsum, calcium carbonate, dolomite, diatomaceous earth, magnesium lime, phosphorus lime, zeolite, silicic anhydride, synthetic calcium silicate, etc.; organic substances of vegetable origin, such as soybean flour, tobacco flour, walnut flour, wheat flour, sawdust, starch, crystalline cellulose, etc.; synthetic or natural polymers such as coumarone resin, petroleum resin, alkyd resin, polyvinyl chloride, polyalkylene glycol, ketone resin, ester gum, copal gum, dammar gum, etc.; waxes such as carnauba wax, beeswax, etc.; or urea and the like.

Examples of suitable liquid carriers include paraffin or naphthene hydrocarbons such as kerosene, mineral oil, spindle oil, white oil, etc.; aromatic hydrocarbons such as xylene, ethylbenzene, cumene, methylnaphthalene, etc.; chlorinated hydrocarbons such as trichloroethylene, monochlorobenzene, o-chlorotoluene, etc.; ethers such as dioxane, tetrahydrofuran, etc.; ketones such as acetone, methyl ethyl ketone, diisobutyl ketone, cyclohexanone, acetophenone, isophorone, etc.; esters such as ethyl acetate, amyl acetate, ethylene glycol acetate, diethylene glycol acetate, dibutyl maleate, diethyl succinate, etc.; alcohols such as methanol, n-hexanol, ethylene glycol, diethylene glycol, cyclohexanol, benzyl alcohol, etc.; ether alcohols such as ethylene glycol ethyl ether, diethylene glycol butyl ether, etc.; polar solvents such as dimethylformamide, dimethylsulfoxide, etc.; and water.

In addition, surfactants and other auxiliary agents may be used for various purposes such as emulsification, dispersion, humidification, spreading, dilation, combination, destruction control, stabilization, improvement of flowability, prevention of corrosion, prevention of freezing, etc., of the compounds of the invention.

As the surfactant, there may be used one of any types among nonionic, anionic, cationic and amphoteric surfactants. Usually, nonionic and/or anionic surfactants are used.

As suitable nonionic surfactants there can be mentioned, for example, additive polymerization products of ethylene oxide with higher alcohols such as lauryl alcohol, stearyl alcohol, oleyl alcohol, etc.; additive polymerization products of ethylene oxide with alkylnaphthols such as butylnaphthol, octylnaphthol, etc.; additive polymerization products of ethylene oxide with higher fatty acids such as palmitic acid, stearic acid, oleic acid, etc.; esters of higher fatty acids and polyhydric alcohols such as sorbitan, and additive polymerization products of ethylene oxide therewith; etc.

As suitable anionic surfactants there can be mentioned, for example, salts of alkyl sulfuric acid ester such as sodium laurylsulfate, amine salts of sulfuric acid ester of oleyl alcohol, etc., alkyl sulfonate salts such as sodium dioctyl sulfosuccinate, sodium 2-ethylhexenesulfonate, etc., arylsulfonate salts such as sodium isopropyl naphthalenesulfonate, sodium methylenebisnaphthalenesulfonate, etc., and the like.

Further, for the purpose of improving the properties of the formulations, i.e. to enhance the effects and so forth, the herbicides of this invention may be used in combination with polymers and other auxiliary agents such as casein, gelatin, albumin, glue, sodium alginate, carboxymethylcellulose, methylcellulose, hydroxyethylcellulose, poly(vinyl alcohol), etc.

The above-described carriers or various auxiliary agents are used singly or in combination with others depending upon the purposes of the compositions, taking into consideration, for instance, the forms of the formulation, the conditions of application, etc.

The contents of active ingredients in the various formulations of this invention thus prepared may vary widely depending upon the form of the formulation; however, a suitable content of active ingredient is generally within the range of 0.1 to 99% by weight, and preferably within the range of 1 to 80% by weight.

In the case of a wettable powder, the formulate prepared generally contains active ingredient compounds in the range of about 25 to 90%, with the remaining ingredients being solid carriers and dispersion wetting agents. If necessary, colloid protection agents, defoaming agents, and so forth may be added thereto.

In the case of granules, the formulate contains active ingredient compounds usually in the range of about 1 to 35% by weight, with the remainder being solid carriers and surfactants. The active ingredient compounds may be mixed with solid carriers uniformly, or fixed to or adsorbed on the surfaces of solid carriers uniformly. It is preferred that the diameter of the granules is within the range of about 0.2 to 1.5 mm.

In the case of an emulsifiable concentrate, the formulate contains active ingredient compounds usually in the range of about 5 to 30% by weight, and, in addition, about 5 to 20% by weight of emulsifiers, with the remainder being liquid carriers. If necessary, spreading agents and anticorrosive agents may be added thereto.

In the case of a flowable composition, the formulate contains active ingredient compounds usually in the range of about 5 to 50% by weight, and, in addition, about 3 to 10% by weight of dispersion wetting agents, with the remainder being water. If necessary, protective colloid agents, preservatives, defoaming agents, etc. may be added thereto.

The compounds of the present invention may be used as herbicides as they are or in any of the forms of formulation, i.e. the compositions, described above. Thus, the present compounds may be used to control the growth of weeds by applying them, in herbicidally effective amounts, to the weeds or to the locus in which they grow.

The herbicides of the present invention may be applied in effective amounts to various lands to be protected, for example, farming lands such as paddy fields and upland fields, or non-farming lands, prior to germination of weeds or to the weeds in various stages from pre-germination to growing stage.

The dose is generally, expressed as amount of active ingredients, in the range of from about 0.1 to about 10,000 g/ha, preferably from about 1 to about 5,000 g/ha. The application doses may be varied properly depending upon the species of weeds being targeted and their growth stages, application sites, weather, etc.

Next, several embodiments of the preparation of the compounds of this invention will be explained in detail in the synthetic Examples which follow. These Examples are given for the purpose of illustration only and are not to be construed as limiting the invention in any way.

EXAMPLE 1

Preparation of 6-acetyloxymethyl-2,2-dimethyl-5-phenyl-2H,4H-1,3-dioxin-4-one (Compound No. 241)

A mixture of 5-phenyl-2,2,6-trimethyl-2H,4H-1,3-dioxin-4-one (11.0 g), N-succinamide bromide (9.9 g) and 2,2'- azobis(isobutyronitrile) (0.25 g) was suspended in carbon tetrachloride (250 ml), and was allowed to keep stirring for 30 minutes with lighting (tungsten lamp, 300 W). The reaction mixture was cooled, filtered, and dried by evaporating the solvent. The crude product was recrystallized from hexane/isopropyl ether to afford 6-bromomethyl-2,2-dimethyl-5-phenyl-2H,4H-1,3-dioxin-4-one (14.59 g, yield 97%).

Then, this product (7.05 g) and sodium acetate (3.9 g) were suspended in dimethylformamide (45 ml), and allowed to react with stirring at 70° C. for 2 hours. The reaction mixture was poured into water, and the product was extracted with ethyl acetate. The organic layer was rinsed with saturated saline solution and dried with magnesium sulfate, and the solvent was evaporated. The crude product was purified by silica gel chromatography to afford the captioned compound (5.28 g, yield 81%).

EXAMPLE 2

Preparation of 6-acetyloxymethyl-3-(1-methyl-1-phenylethyl)-5-phenyl-2,3-dihydro-4H-1,3-oxazin-4-one (Compound No. 66) (Method A)

A mixture of 6-acetyloxymethyl-2,2-dimethyl-5-phenyl-2H,4H-1,3-dioxin-4-one (Compound No. 241, 5.0 g) and N-methylene-1-methyl-1-phenylethylamine (2.9 g) was dissolved in xylene (40 ml) and allowed to react by refluxing for 30 minutes. The reaction mixture was purified by silica gel chromatography to afford the captioned compound (yield 72%).

EXAMPLE 3

Preparation of 6-hydroxymethyl-3-(1-methyl-1-phenylethyl)-5-phenyl-2,3-dihydro-4H-1,3-oxazin-4-one (Compound No. 53)

6-Acetyloxymethyl-3-(1-methyl-1-phenylethyl)-5-phenyl-2,3-dihydro-4H-1,3-oxazin-4-one (Compound No. 66, 4.99 g) was dissolved in methanol (55 ml), and an aqueous solution (14 ml) of potassium carbonate (1.3 g) was added slowly thereto. This mixture was allowed to react by stirring at room temperature for one hour. Methanol was removed by evaporation, and the residue was acidified with 2N hydrochloric acid, and extracted with ethyl acetate. The organic layer was rinsed with saturated saline solution, and dried with magnesium sulfate to afford the captioned product (4.0 g, yield 91%).

EXAMPLE 4

Preparation of 6-methoxymethyl-3-(1-methyl-1-phenylethyl)-5-phenyl-2,3-dihydro-4H-1,3-oxazin-4-one (Compound No. 114)

Sodium hydride (60% in oil, 0.11 g) was suspended in diformaldahyde (2 ml), cooled with ice; then a dimethylformamide solution (6 ml) of 6-hydroxymethyl-3-(1-methyl-1-phenylethyl)-5-phenyl-2,3-dihydro-4H-1,3-oxazin-4-one (Compound No. 53, 0.8 g) was added slowly thereto. After stirring the mixture, methyl iodide (0.71 g) was added, and the mixture was stirred again at room temperature. The reaction mixture was poured into water, and extracted with ethyl acetate. The organic layer was rinsed with saturated saline solution, and dried with magnesium sulfate, and the solvent was evaporated. The crude product was purified by silica gel chromatography to afford the captioned compound (0.56 g, yield 67%).

EXAMPLE 5

Preparation of 6-formyl-3-(1-methyl-1-phenylethyl)-5-phenyl-2,3-dihydro-4H-1,3-oxazin-4-one (Compound No. 121)

Pyridinium chlorochromate (4.70 g) was suspended in dichloromethane (20 ml), and a dichloromethane solution (27 ml) of 6-hydroxymethyl-3-(1-methyl-1-phenylethyl)-5-phenyl-2,3-dihydro-4H-1,3-oxazin-4-one (Compound No. 53, 4.70 g) was added thereto at room temperature. After stirring for about 9 hours, a large amount of ether was added and separated by decantation. The organic layer was dried with magnesium sulfate and the solvent was evaporated. The crude product was purified by silica gel chromatography to afford the captioned compound (4.47 g, yield 96%).

EXAMPLE 6

Preparation of 6-Difluoromethyl-3-(1-methyl-1-phenylethyl)-5-phenyl-2,3-dihydro-4H-1,3-oxazin-4-one (Compound No. 34)

Diethylaminosulfate trifluoride (0.51 g) was dissolved in dichloromethane (2 ml); then, a dichloromethane solution (5 ml) of 6-formyl-3-(1-methyl-1-phenylethyl)-5-phenyl-2,3-dihydro-4H-1,3-oxazin-4-one (Compound No. 121, 1.0 g) was added dropwise at room temperature, and the mixture was allowed to react, with stirring. The solvent was removed by evaporation, and the captioned compound was obtained by purification using silica gel chromatography (0.70 g, yield 66%).

EXAMPLE 7

Preparation of 6-Hydroxyiminomethyl-3-(1-methyl-1-phenylethyl)-5-phenyl-2,3-dihydro-4H-1,3-oxazin-4-one (Compound No. 134)

6-Formyl-3-(1-methyl-1-phenylethyl)-5-phenyl-2,3-dihydro-4H-1,3-oxazin-4-one (Compound No. 121, 2.87 g) was dissolved in ethanol (30 ml), and an aqueous solution (15 ml) of hydroxylamine hydrochloric acid (0.65 g) and sodium acetate (1.30 g) was added slowly thereto at room temperature. After stirring for one hour, ethanol was removed by evaporation, and filtered after adding water. The solid product obtained was rinsed with water and dried to afford the captioned compound (2.59 g, yield 86%).

EXAMPLE 8

Preparation of 6-Acetyloxymethyl-3-[1-methyl-1-(3,5-dichlorophenyl)ethyl]-5-phenyl-2,3-dihydro-4H-1,3-oxazin-4-one (Compound No. 69)

6-Acetyloxymethyl-2,2-dimethyl-5-phenyl-2H, 4H-1,3-dioxin-4-one (Compound No. 241, 17.1 g) was mixed with N-ethylene-1-methyl-1-(3,5-dichlorophenyl)ethylamine (14.7 g), and xylene (120 ml) was added thereto. After refluxing for one hour, the solvent was removed by evaporation, and the crude product was recrystallized from a mixture of hexane and ethyl acetate to afford the captioned compound (22.83 g, yield 85%).

Preparation of 6-Fluoromethyl-3-[1-methyl-1-(3,5-dichlorophenyl)ethyl]-5-phenyl-2,3-dihydro-4H-1,3-oxazin-4-one (Compound No. 4)

Diethylaminosulfate trifluoride (0.60 g) was dissolved in dichloromethane (3 ml), and a dichloromethane solution (7 ml) of 6-hydroxymethyl-3-[1-methyl-1-(3,5-dichlorophenyl)ethyl]-5-phenyl-2,3-dihydro-4H-1,3-oxazin-4-one (Compound No. 55, 1.40 g) was added dropwise at −63° C.

After warming to room temperature by stirring for 30 minutes, the reaction mixture was fractionated, and the organic layer was rinsed with water and dried with magnesium sulfate. The solvent was removed by evaporation, and the crude product was purified by silica gel chromatography to afford the captioned compound (0.99 g, yield 70%).

Preparation of 6-Acetyloxyiminomethyl-3-[1-methyl-1-(3,5-dichlorophenyl)ethyl]-5-phenyl-2, 3-dihydro-4H-1,3-oxazin-4-one (Compound No. 147)

A mixture of 6-hydroxyiminomethyl-3-[1-methyl-1-(3,5-dichlorophenyl)ethyl]-5-phenyl-2,3-dihydro-4H-1,3-oxazin-4-one (Compound No. 135, 0.60 g) and anhydrous acetic acid (2 ml) was stirred at room temperature for 4 hours. The reaction mixture was poured into water, and extracted with ethyl acetate. The organic layer was rinsed with saturated saline solution, and dried with magnesium sulfate. The solvent was removed by evaporation, and the crude product was purified by silica gel chromatography to afford the captioned compound (0.54 g, yield 94%).

Preparation of 6-Cyano-3-[1-methyl-1-(3,5-dichlorophenyl)ethyl]-5-phenyl-2,3-dihydro-4H-1,3-oxazin-4-one (Compound No. 167)

6-Hydroxyiminomethyl-3-[1-methyl-1-(3,5-dichlorophenyl)ethyl]-5-phenyl-2,3-dihydro-4H-1,3-oxazin-4-one (Compound No. 135, 0.50 g), triphenylphosphine (0.33 g), carbon tetrachloride (0.19 g) and triethylamine (0.13 g) were mixed, and dichloromethane (5 ml) was added thereto. The mixture was refluxed for two and one-half hours. The reaction mixture was rinsed with water and dried with magnesium sulfate, then the solvent was removed by evaporation and the crude product was purified by silica gel chromatography to afford the captioned compound (0.39 g, yield 82%).

Preparation of 6-Trifluoromethyl-3-[1-methyl-1-(3,5-dichlorophenyl)ethyl]-5-phenyl-2,3-dihydro-4H-1,3-oxazin-4-one (Compound No. 49) (Method B)

Ethyl 2-trifluoroacetyl-2-phenylacetate (1.30 g) and N-methylene-1-methyl-1-(3,5-dichlorophenyl)ethylamine (1.19 g) were mixed, and xylene (10 ml) was added thereto. The mixture was allowed to react by refluxing for 30 minutes. The solvent was removed by evaporation, and the crude product was recrystallized from a mixture of hexane and ethyl acetate to afford the captioned compound (1.80 g, yield 84%).

Preparation of 6-Hydroxymethyl-2,2-dimethyl-5-phenyl-2H,4H-1,3-dioxin-4-one (Compound No. 236)

6-Acetyloxymethyl-2,2-dimethyl-5-phenyl-2H,4H-1,3-dioxin-4-one (Compound No. 241, 7.46 g) was dissolved in methanol (108 ml), and cooled with ice; then, an aqueous solution (27 ml) of potassium carbonate (2.42 g) was added slowly thereto.

After stirring for 30 minutes, methanol was removed by evaporation, the residue was acidified with 2N hydrochloric acid and the mixture was filtered. The crude product was recrystallized from a mixture of hexane and ethyl acetate to afford the captioned compound (3.84 g, yield 61%).

Preparation of 6-Formyl-2,2-dimethyl-5-phenyl-2H, 4H-1,3-dioxin-4-one (Compound No. 246)

Pyridinium chlorochromate (1.29 g) was suspended into dichloromethane (8 ml), then a dichloromethane suspension (3 ml) of 6-hydroxymethyl-2,2-dimethyl-5-phenyl-2H,4H-1,3-dioxin-4-one (Compound No. 236, 0.70 g) was added thereto at room temperature. After stirring for 5 hours, a large amount of ether was added and extracted by decantation. The organic layer was dried with magnesium sulfate, the solvent was removed by evaporation, and the crude product was purified by silica gel chromatography to afford the captioned compound (0.43 g, yield 67%).

The melting points and δ-values of H-NMR of the compounds prepared in the preceding Examples and the compounds prepared by similar preparation methods are shown in Table 3 below.

TABLE 3

| Compd. No. | $^1$H-NMR δ (ppm) Solvent CDCl$_3$ TMS = 0 ppm | Melting Point (°C.) |
| --- | --- | --- |
| 1 | 1.84 (s, 6H), 4.81 (d, 2H), 5.18 (s, 2H), 7.23–7.44 (m, 10H) | 82.4–85.0 |
| 4 | 1.75 (s, 6H), 4.84 (d, 2H), 5.37 (s, 2H), 7.20–7.38 (m, 8H) | 96.1–99.5 |
| 34 | 1.84 (s, 6H), 5.24 (s, 2H), 6.01 (t, 1H), 7.22–7.43 (m, 10H) | 78.3–80.3 |
| 36 | 1.76 (s, 6H), 5.43 (s, 2H), 6.03 (t, 1H), 7.20–7.39 (m, 8H) | 112.5–115.8 |
| 48 | 1.85 (s, 6H), 5.21 (s, 2H), 7.23–7.43 (m, 10H) | Oily Substance |
| 49 | 1.76 (s, 6H), 5.42 (s, 2H), 7.20–7.25 (m, 5H), 7.32–7.38 (m, 3H) | 121.6–123.9 |
| 53 | 1.84 (s, 6H), 4.17 (d, 2H), 5.15 (s, 2H) 7.21–7.44 (m, 10H) | 156.5–159.5 |
| 55 | 1.74 (s, 6H), 4.19 (s, 2H), 5.34 (s, 2H), 7.19–7.36 (m, 8H) | 132.4–136.7 |
| 66 | 1.83 (s, 6H), 2.03 (s, 3H), 4.61 (s, 2H), 5.14 (s, 2H), 7.21–7.43 (m, 10H) | Oily Substance |
| 69 | 1.74 (s, 6H), 3.33 (s, 3H), 3.98 (s, 2H), 5.35 (s, 2H), 7.19–7.36 (m, 8H) | 115.0–117.0 |
| 114 | 1.83 (s, 6H), 3.30 (s, 3H), 3.95 (s, 2H), 5.17 (s, 2H), 7.20–7.43 (m, 10H) | Oily Substance |
| 116 | 1.74 (s, 6H), 3.33 (s, 3H), 3.98 (s, 2H), 5.36 (s, 2H), 7.20–7.36 (m, 8H) | Oily Substance |
| 121 | 1.85 (s, 6H), 5.23 (s, 2H), 7.22–7.46 (m, 10H), 9.36 (s, 1H) | 94.0–97.7 |
| 122 | 1.77 (s, 6H), 5.40 (s, 2H), 7.22 (s, 3H), 7.41 (s, 5H), 9.38 (s, 1H) | 98.9–102.0 |
| 134 | 1.85 (s, 6H), 5.23 (s, 2H), 7.21–7.43 (m, 10H), 7.55 (s, 1H), 8.06 (s, 1H) | 176.0–181.5 (decomposed) |
| 135 | 1.76 (s, 6H), 5.41 (s, 2H), 7.20–7.38 (m, 8H), 7.57 (s, 1H), 8.15 (s, 1H) | 187.0–197.0 (decomposed) |
| 147 | 1.76 (s, 6H), 2.16 (s, 3H), 5.45 (s, 2H), 7.20–7.40 (m, 8H), 7.78 (s, 1H) | 177.7–180.0 |
| 160 | 1.75 (s, 6H), 4.00 (s, 3H), 5.43 (s, 2H), 7.20–7.35 (m, 8H), 7.51 (s, 1H) | 129.5–132.5 |
| 164 | 1.84 (s, 6H), 5.20 (s, 2H), 7.26–7.47 (m, 10H) | 141.5–145.2 |
| 167 | 1.76 (s, 6H), 5.38 (s, 2H), 7.22 (s, 3H), 7.41 (s, 5H) | 123.3–127.5 |
| 236 | 1.82 (s, 6H), 1.89 (t, 1H), 4.20 (d, 2H), 7.28–7.43 (m, 5H) | 94.0–96.5 |
| 241 | 1.79 (s, 6H), 2.05 (s, 3H), 4.62 (s, 2H), 7.25–7.42 (m, 5H) | Oily Substance |
| 246 | 1.84 (s, 6H), 7.40–7.50 (m, 5H), 9.46 (s, 1H) | 78.0–80.8 |

Several representative herbicidal compositions using the compounds of this invention are shown below. In these formulations, all "parts" are by weight.

FORMULATION EXAMPLE 1

(Emulsifiable Concentrate)

| | |
|---|---|
| Compound No. 147 | 20 parts |
| Xylene | 50 parts |
| Cyclohexane | 20 parts |
| Calcium dodecylbenzenesulfonate | 5 parts |
| Polyoxyethylenestyrylphenyl ether | 5 parts |

The above substances were mixed and dissolved uniformly to obtain 100 parts of an emulsifiable concentrate formulate.

FORMULATION EXAMPLE 2

(Wettable Powder)

| | |
|---|---|
| Compound No. 147 | 20 parts |
| Clay | 70 parts |
| Calcium ligninsulfonate | 7 parts |
| Condensate of alkylnaphthalenesulfonic acid and formaldehyde | 3 parts |

The above substances were mixed and pulverized using a jet mill to obtain 100 parts of a wettable powder formulate.

FORMULATION EXAMPLE 3

(Flowable)

| | |
|---|---|
| Compound No. 147 | 20 parts |
| Sodium di-(2-ethylhexyl)sulfosuccinate | 2 parts |
| Polyoxyethylene nonylphenyl ether | 0.5 parts |
| Defoaming agent | 5 parts |
| Propylene glycol | 5 parts |
| Water | 70.5 parts |

The above substances were mixed and pulverized uniformly using a wet ball mill to obtain 100 parts of a flowable formulate.

The herbicidal effects of the compounds of the present invention are illustrated by the following test examples.

TEST EXAMPLE 1

(Paddy Field Soil Treatment)

Suitable amounts of water and chemical fertilizer were added to paddy field soil. This soil was filled into 130 cm² plastic pots, followed by kneading to convert it to the state of a paddy field, to which a stock of paddy field rice plant (variety: Koshihikari) composing a pair of two seedlings, that had been grown in advance in a greenhouse to a stage of two leaves, were transplanted to each pot in a population of one stock per pot. Further, in each pot, there were added predetermined amounts of seeds of Nobie (*Echinochloa orizicola*), Konagi (*Monochoria vaginalis var. plantaginea*), Azena (*Lindernia procumbens*) and Hotarui (*Scirpus juncoides var. hotarui*), respectively, and water was added to a depth of 3 cm. On the next day, wettable powder formulates were prepared by the method described in Formulation Example 2, and diluted with a suitable amount of water up to a concentration of active ingredient of 5 kg or 1 kg per ha. The diluted formulate was applied by dropping with a pipette.

After 21 days from the application of the chemicals, the herbicidal effects on each weed and the phytotoxicity on the paddy field rice plants were assessed according to the following criteria. The results which were obtained are shown in Table 4.

| | Evaluation criteria (11 ranks) | |
|---|---|---|
| Score | Herbicidal effects: Ratio of killed weeds compared to the control (%) | Phytotoxicity to crop: Ratio of injured plants compared to the control (%) |
| 0 | 0 | Same as the left column |
| 1 | Above 0 to 10 | |
| 2 | Above 10 to 20 | |
| 3 | Above 20 to 30 | |
| 4 | Above 30 to 40 | |
| 5 | Above 40 to 50 | |
| 6 | Above 50 to 60 | |
| 7 | Above 60 to 70 | |
| 8 | Above 70 to 80 | |
| 9 | Above 80 to 90 | |
| 10 | Above 90 to 100 (withered) | |

TABLE 4

| Compd. No. | Active ingredient Dose g ai/ha | Herbicidal effects | | | | Phyto-toxicity |
|---|---|---|---|---|---|---|
| | | Nobie | Konagi | Azena | Hotarui | Rice plant |
| 4 | 1000 | 10 | 10 | 10 | 10 | 2 |
| | 5000 | 10 | 10 | 10 | 10 | 10 |
| 34 | 1000 | 10 | 10 | 10 | 10 | 0 |
| | 5000 | 10 | 10 | 10 | 10 | 2 |
| 49 | 1000 | 10 | 10 | 10 | 10 | 0 |
| | 5000 | 10 | 10 | 10 | 10 | 0 |
| 69 | 1000 | 10 | 10 | 10 | 10 | 10 |
| | 5000 | 10 | 10 | 10 | 10 | 10 |
| 147 | 1000 | 10 | 10 | 10 | 10 | 6 |
| | 5000 | 10 | 10 | 10 | 10 | 7 |

Note:
Nobie: *Echinochloa orizicola*
Konagi: *Monochoria vaginalis var. plantaginea*
Azena: *Lindernia procumbens*
Hotarui: *Scirpus juncoides var. hotarui*

TEST EXAMPLE 2

(Paddy Field Foliar Application)

Paddy field soil was filled into 130 cm² plastic pots, and suitable amounts of water and chemical fertilizers were added thereto, and kneaded to convert it to the state of a paddy field. A stock of paddy field rice plant (variety: Koshihikari) composing a pair of two seedlings, that had been grown in advance in a greenhouse to a stage of two leaves, were transplanted into each pot in a population of one stock per pot. Further, in each pot, there were sown predetermined amounts of seeds of Nobie (*Echinochloa orizicola*), Konagi (*Monochoria vaginalis var. plantaginea*), Azena (*Lindernia procumbens*) and Hotarui (*Scirpus juncoides var. hotarui*), respectively, and water was added to a depth of 3 cm.

After having grown the plants in a greenhouse until Nobie (*Echinochloa orizicola*) reached a stage of 1.5 leaves, wettable powder formulates were prepared by the method described in Formulation Example 2, and diluted with a suitable amount of water up to a concentration of the active ingredient of 5 kg or 1 kg per ha. The diluted formulate was applied by dropping with a pipette.

After 21 days from the application of the chemicals, herbicidal effects on each weed and phytotoxicity on paddy field rice plants were assessed based on the criteria as described in the Test Example 1. The results obtained are shown in Table 5.

TABLE 5

| Compd. No. | Active ingredient Dose g ai/ha | Herbicidal effects Nobie | Konagi | Azena | Hotarui | Phytotoxicity Rice plant |
|---|---|---|---|---|---|---|
| 4 | 1000 | 10 | 10 | 10 | 9 | 3 |
|  | 5000 | 10 | 10 | 10 | 9 | 8 |
| 34 | 1000 | 9 | 9 | 10 | 10 | 0 |
|  | 5000 | 10 | 10 | 10 | 10 | 0 |
| 49 | 1000 | 10 | 4 | 10 | 10 | 0 |
|  | 5000 | 10 | 9 | 10 | 10 | 0 |
| 69 | 1000 | 10 | 10 | 10 | 10 | 10 |
|  | 5000 | 10 | 10 | 10 | 10 | 10 |
| 147 | 1000 | 10 | 10 | 10 | 10 | 3 |
|  | 5000 | 10 | 10 | 10 | 10 | 8 |

Note:
Nobie: *Echinochloa orizicola*
Konagi: *Monochoria vaginalis* var. *plantaginea*
Azena: *Lindernia procumbens*
Hotarui: *Scirpus juncoides* var. *hotarui*

TEST EXAMPLE 3

(Upland Soil Application)

Upland soil was filled into 130 cm² plastic pots, in which there were sown predetermined amounts of seeds of Nobie (*Echinochloa crus-galli*), Mehishiba (*Digitaria ciliaris*) and Enokorogusa (*Setaria viridis*), respectively, and soil was placed thereon to a thickness of 1 cm.

On the day next to sowing, wettable powder formulates were prepared by the method described in Formulation Example 2, and diluted with a suitable amount of water up to a concentration of active ingredient of 5 kg or 1 kg per ha. The diluted formulate was sprayed uniformly over the surface of the soil.

After 21 days from the application of the chemicals, herbicidal effects on each weed were assessed based on the criteria described in the Test Example 1. Results obtained are shown in Table 6.

TABLE 6

| Compd. No. | Active ingredient Dose g ai/ha | Herbicidal effects Nobie | Mehishiba | Enokorogusa |
|---|---|---|---|---|
| 4 | 1000 | 10 | 10 | 9 |
|  | 5000 | 10 | 10 | 10 |
| 34 | 5000 | 10 | 10 | 10 |
| 49 | 5000 | 8 | 10 | 10 |
| 69 | 1000 | 10 | 10 | 10 |
|  | 5000 | 10 | 10 | 10 |
| 147 | 1000 | 10 | 10 | 10 |
|  | 5000 | 10 | 10 | 10 |

Note:
Nobie: *Echinochloa crus-galli*
Mehishiba: *Digitaria ciliaris*
Enokorogusa: *Setaria viridis*

The compounds of the present invention having formula (I) show excellent herbicidal effects at very low doses over a wide range from germination to growth stage of paddy field annual weeds such as Hie (*Echinochloa orizicola*), Tamagayatsuri (*Cyperus difformis*), Konagi (*Monochoria vaginalis* var. *plantaginea*), Kikashigusa (*Rotala indica* var. *uliginosa*), Azena (*Lindernia procumbens*), Abunome (*Dopatrium junceum*) and the like, and paddy field perennial weeds such as Hotarui (*Scirpus juncoides* var. *hotarui*), Matsubai (*Eleocharis acicularis* var *longiseta*), Heraomodaka (*Alisma canaliculatum*), Mizugayatsuri (*Cyperus serotinus*) and the like, and also show high safety for transplanted rice plants and directly sown rice plants in either paddy or upland fields.

In addition, the instant compounds show high herbicidal effects, in soil or on foliar application, on various upland broadleaf weeds such as Tade (*Persicaria longiseta*), Aobiyu (*Amaranthus viridis*), Shiroza (*Chenopodium album*) and the like, annual and perennial Cyperus weeds such as Hamasuge (*Cyperus rotundus*), Kihamasuge (*Cyperus esculantus*), Himekugu (*Cyperus brevifolius* var. *leiolepis*), Kayatsurigusa (*Cyperus microiria*), Kogomegayatsuri (*Cyperus iria*) and the like, and upland gramineous weeds such as Hie (*Echinochloa crus-galli*), Mehishiba (*Digitaria ciliaris*), Enokorogusa (*Setaria viridis*), Suzumenokatabira (*Poa annua*), Johnsongrass (*Sorghum halepense*), Wild oat (*Avena sativa*), Suzumenoteppo (*Alopecurus aequalis* var *amurensis*), and the like, and they also show characteristically high safety for crops such as soybean, cotton, sugar beet, rape, sunflower, maize, upland rice, wheat and so forth.

The compounds of the present invention can be used not only in paddy and upland fields but also in orchards, mulberry fields, turf, and non-farming lands. Furthermore, by mixing the compounds of this invention with already known compounds, they show complete herbicidal effects on weeds which are difficult to be controlled by each of the compounds applied singly, and effectively control various weeds by synergistic herbicidal effects at doses at which single compound hardly can control. In addition, the compounds of the present invention show high safety for crops such as paddy field rice, soybean, cotton, sugar beet, rape, sunflower, maize, upland rice, wheat and the like; therefore, they can provide herbicides which are very useful in agriculture.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the formula:

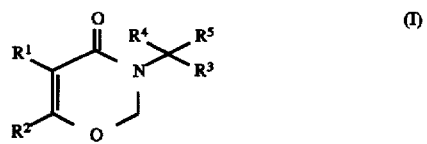

wherein:

R¹ is a lower alkyl radical, a lower alkenyl radical, a lower alkynyl radical, an aryl radical which is unsubstituted or substituted, or an aralkyl radical which is unsubstituted or substituted;

R² is a lower hydroxyalkyl radical, a lower alkoxyalkyl radical, a lower acyloxyalkyl radical, a formyl radical, a hydroxyiminomethyl radical, a lower alkoxyiminomethyl radical, a lower acyloxyiminomethyl radical, a cyano radical or a lower alkoxycarbonyl radical;

R³ is a lower alkyl radical, an aryl radical which is unsubstituted or substituted, or an aralkyl radical which is unsubstituted or substituted; and R⁴ and R⁵, independently, are each a lower alkyl radical; or R⁴ and R⁵, taken together with the carbon atom to which they are bonded, combine to form a 3- to 8-membered carbocyclic ring which is unsubstituted or is substituted by 1 or more lower alkyl radicals.

2. A method for controlling the growth of weeds at a locus comprising applying to said weeds or to the locus in which they grow a herbicidally effective amount of a compound having the formula:

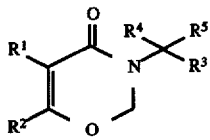
(I)

wherein:

R¹ is a lower alkyl radical, a lower alkenyl radical, a lower alkynyl radical, an aryl radical which is unsubstituted or substituted, or an aralkyl radical which is unsubstituted or substituted;

R² is a lower hydroxyalkyl radical, a lower alkoxyalkyl radical, a lower acyloxyalkyl radical, a formyl radical, a hydroxyiminomethyl radical, a lower alkoxyiminomethyl radical, a lower acyloxyiminomethyl radical, a cyano radical or a lower alkoxycarbonyl radical;

R³ is a lower alkyl radical, an aryl radical which is unsubstituted or substituted, or an aralkyl radical which is unsubstituted or substituted; and R⁴ and R⁵, independently, are each a lower alkyl radical; or R⁴ and R⁵, taken together with the carbon atom to which they are bonded, combine to form a 3- to 8-membered carbocyclic ring which is unsubstituted or is substituted by 1 or more lower alkyl radicals.

3. A compound having the formula:

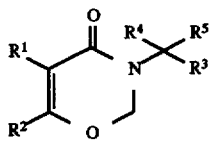
(I)

wherein:

R¹ is a lower alkyl radical; a lower alkenyl radical; a lower alkynyl radical; an aryl radical which is phenyl or naphthyl, each of which is unsubstituted or is substituted by one or more members selected from the group consisting of halogen, lower alkyl, lower alkoxy, lower haloalkyl, lower haloalkoxy and nitro; or an aralkyl radical wherein the alkyl portion has 1 to 4 carbon atoms, and wherein the aryl portion is phenyl or naphthyl, each of which is unsubstituted or is substituted by one or more members selected from the group consisting of halogen, lower alkyl, lower alkoxy, lower haloalkyl, lower haloalkoxy and nitro;

R² is a lower hydroxyalkyl radical, a lower alkoxyalkyl radical, a lower acyloxyalkyl radical, a formyl radical, a hydroxyiminomethyl radical, a lower alkoxyiminomethyl radical, a lower acyloxyiminomethyl radical, a cyano radical or a lower alkoxycarbonyl radical;

R³ is a lower alkyl radical; an aryl radical which is phenyl or naphthyl, each of which is unsubstituted or is substituted by one or more members selected from the group consisting of halogen, lower alkyl, lower alkoxy, lower haloalkyl, lower haloalkoxy and nitro; or an aralkyl radical wherein the alkyl portion has 1 to 4 carbon atoms, and wherein the aryl portion is phenyl or naphthyl, each of which is unsubstituted or is substituted by one or more members selected from the group consisting of halogen, lower alkyl, lower alkoxy, lower haloalkyl, lower haloalkoxy and nitro; and R⁴ and R⁵, independently, are each a lower alkyl radical; or R⁴ and R⁵ are taken together with the carbon atom to which they are bonded to form a 3- to 8-membered saturated carbocyclic ring which is unsubstituted or is substituted by 1 or more lower alkyl radicals.

4. The compound according to claim 3, having the formula:

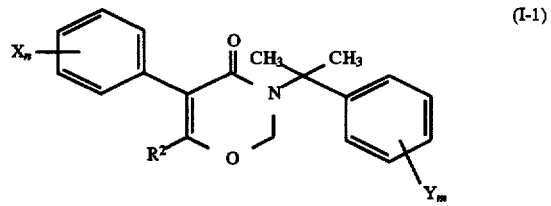
(I-1)

wherein:

X is halogen or lower alkyl;

Y is halogen or lower haloalkyl;

n is 0 or 1; and m is 0, 1 or 2, provided that when m is 2, then the substituents represented by Y can be the same or different.

5. A method for controlling the growth of weeds at a locus comprising applying to said weeds or to the locus in which they grow a herbicidally effective amount of a compound as claimed in claim 3.

6. A method for controlling the growth of weeds at a locus comprising applying to said weeds or to the locus in which they grow a herbicidally effective amount of a compound as claimed in claim 4.

7. A compound having the formula:

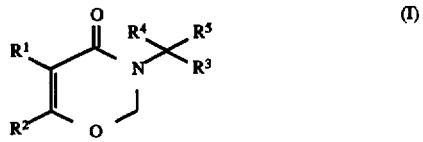
(I)

wherein:

R¹ is a lower alkyl radical; a lower alkenyl radical; a lower alkynyl radical; an aryl radical which is phenyl or naphthyl, each of which is unsubstituted or is substituted by one or more members selected from the group consisting of halogen, lower alkyl, lower alkoxy, lower haloalkyl, lower haloalkoxy and nitro; or an aralkyl radical wherein the alkyl portion has 1 to 4 carbon atoms, and wherein the aryl portion is phenyl or naphthyl, each of which is unsubstituted or is substituted by one or more members selected from the group consisting of halogen, lower alkyl, lower alkoxy, lower haloalkyl, lower haloalkoxy and nitro;

R² is a formyl radical, a hydroxyiminomethyl radical, a lower alkoxyiminomethyl radical, a lower acyloxyiminomethyl radical, a cyano radical or a lower alkoxycarbonyl radical;

R³ is a lower alkyl radical; an aryl radical which is phenyl or naphthyl, each of which is unsubstituted or is substituted by one or more members selected from the group consisting of halogen, lower alkyl, lower alkoxy, lower haloalkyl, lower haloalkoxy and nitro; or an aralkyl radical wherein the alkyl portion has 1 to 4 carbon atoms, and wherein the aryl portion is phenyl or naphthyl, each of which is unsubstituted or is substituted by one or more members selected from the group consisting of halogen, lower alkyl, lower alkoxy, lower haloalkyl, lower haloalkoxy and nitro; and $R^4$ and $R^5$, independently, are each a lower alkyl radical; or $R^4$ and $R^5$ are taken together with the carbon atom to which they are bonded to form a 3- to 8-membered saturated carbocyclic ring which is unsubstituted or is substituted by 1 or more lower alkyl radicals.

8. The compound according to claim 7, having the formula:

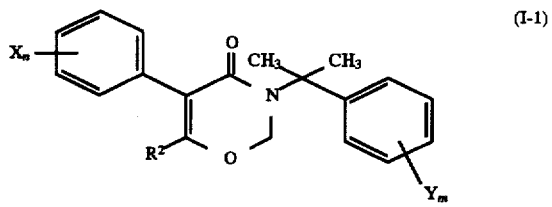

(I-1)

wherein:

X is halogen or lower alkyl;

Y is halogen or lower haloalkyl;

n is 0 or 1; and m is 0, 1 or 2, provided that when m is 2, then the substituents represented by Y can be the same or different.

9. A method for controlling the growth of weeds at a locus comprising applying to said weeds or to the locus in which they grow a herbicidally effective amount of a compound as claimed in claim 7.

10. A method for controlling the growth of weeds at a locus comprising applying to said weeds or to the locus in which they grow a herbicidally effective amount of a compound as claimed in claim 8.

11. A method for controlling the growth of weeds at a crop locus without substantial damage to the crop which is grown at said locus, said method comprising applying to said weeds or to said locus a compound having the formula:

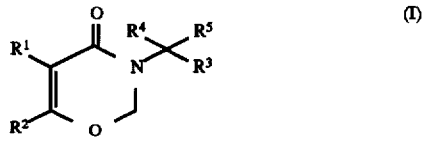

(I)

wherein:

$R^1$ is a lower alkenyl radical, a lower alkynyl radical, an aryl radical which is unsubstituted or substituted, or an aralkyl radical which is unsubstituted or substituted;

$R^2$ is a lower hydroxyalkyl radical, a lower alkoxyalkyl radical, a lower acyloxyalkyl radical, a formyl radical, a hydroxyiminomethyl radical, a lower alkoxyiminomethyl radical, a lower acyloxyiminomethyl radical, a cyano radical or a lower alkoxycarbonyl radical;

$R^3$ is a lower alkyl radical, an aryl radical which is unsubstituted or substituted, or an aralkyl radical which is unsubstituted or substituted; and $R^4$ and $R^5$, independently, are each a lower alkyl radical; or $R^4$ and $R^5$, taken together with the carbon atom to which they are bonded, combine to form a 3- to 8-membered carbocyclic ring which is unsubstituted or is substituted by 1 or more lower alkyl radicals;

in an amount which is herbicidally effective and which is non-phytotoxic to the crop.

12. The method according to claim 11, wherein, in the compound of formula (I):

$R^1$ is a lower alkyl radical; a lower alkenyl radical; a lower alkynyl radical; an aryl radical which is phenyl or naphthyl, each of which is unsubstituted or is substituted by one or more members selected from the group consisting of halogen, lower alkyl, lower alkoxy, lower haloalkyl, lower haloalkoxy and nitro; or an aralkyl radical wherein the alkyl portion has 1 to 4 carbon atoms, and wherein the aryl portion is phenyl or naphthyl, each of which is unsubstituted or is substituted by one or more members selected from the group consisting of halogen, lower alkyl, lower alkoxy, lower haloalkyl, lower haloalkoxy and nitro;

$R^2$ is a lower alkoxyalkyl radical, a lower acyloxyalkyl radical, a formyl radical, a hydroxyiminomethyl radical, a lower alkoxyiminomethyl radical, a lower acyloxyiminomethyl radical, a cyano radical or a lower alkoxycarbonyl radical;

$R^3$ is a lower alkyl radical; an aryl radical which is phenyl or naphthyl, each of which is unsubstituted or is substituted by one or more members selected from the group consisting of halogen, lower alkyl, lower alkoxy, lower haloalkyl, lower haloalkoxy and nitro; or an aralkyl radical wherein the alkyl portion has 1 to 4 carbon atoms, and wherein the aryl portion is phenyl or naphthyl, each of which is unsubstituted or is substituted by one or more members selected from the group consisting of halogen, lower alkyl, lower alkoxy, lower haloalkyl, lower haloalkoxy and nitro; and $R^4$ and $R^5$, independently, are each a lower alkyl radical; or $R^4$ and $R^5$ are taken together with the carbon atom to which they are bonded to form a 3- to 8-membered saturated carbocyclic ring which is unsubstituted or is substituted by 1 or more lower alkyl radicals.

13. The method according to claim 12, wherein the compound of formula (I) has the formula:

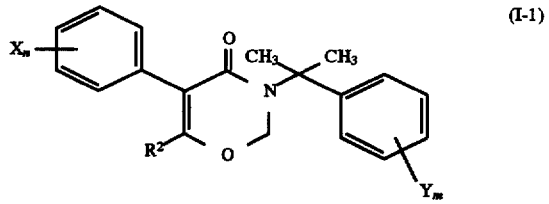

(I-1)

wherein:

X is halogen or lower alkyl;

Y is halogen or lower haloalkyl;

n is 0 or 1; and m is 0, 1 or 2, provided that when m is 2, then the substituents represented by Y can be the same or different.

14. The method according to claim 11, wherein said crop locus comprises a rice paddy field or an upland rice field.

15. The compound according to claim 3, wherein $R^1$ is a branched lower alkyl radical.

16. The compound according to claim 15, wherein $R^1$ is branched alkyl having 3 or 4 carbon atoms.

17. The compound according to claim 16, wherein $R^1$ is isobutyl or isopropyl.

18. The compound according to claim 3, wherein $R^1$ is phenyl or phenyl substituted by halogen or lower alkyl.

19. The compound according to claim 3, wherein $R^3$ is phenyl or 2-naphthyl, each of which is unsubstituted or is substituted by one or two halogen, lower haloalkyl or lower haloalkoxy.

20. The compound according to claim 3, wherein $R^4$ is methyl.

21. The compound according to claim 3, wherein $R^5$ is methyl.

22. The compound according to claim 3, wherein:

$R^1$ is $C_3$–$C_4$ branched alkyl, phenyl, or phenyl substituted by halogen or lower alkyl;

$R^3$ is phenyl or 2-naphthyl, each of which is unsubstituted or is substituted by one or two halogen, lower haloalkyl or lower haloalkoxy;

$R^4$ is methyl; and $R^5$ is methyl.

23. The compound according to claim 8, which is 6-acetyloxyiminomethyl-3-[1-methyl-1-(3,5-dichlorophenyl)ethyl]-5-phenyl-2,3-dihydro-4H-1,3-oxazin-4-one.

24. A herbicidal composition comprising a herbicidally effective amount of a compound of formula (I) as claimed in claim 1 and an agriculturally acceptable inert carrier.

25. A herbicidal composition comprising a herbicidally effective amount of a compound of formula (I) as claimed in claim 3 and an agriculturally acceptable inert carrier.

26. A herbicidal composition comprising a herbicidally effective amount of a compound of formula (I) as claimed in claim 22 and an agriculturally acceptable inert carrier.

27. A herbicidal composition comprising a herbicidally effective amount of a compound of formula (I-1) as claimed in claim 4 and an agriculturally acceptable inert carrier.

28. The composition according to claim 24, comprising from about 0.1 to about 99% by weight of compound of formula (I).

29. The composition according to claim 28, comprising from about 1 to about 80% by weight of compound of formula (I).

30. The composition according to claim 28, which is a wettable powder comprising from about 25 to about 90% by weight of compound of formula (I), the remainder of the composition consisting of one or more solid carriers and one or more dispersion wetting agents.

31. The composition according to claim 29, which is a granule comprising from about 1 to about 35% by weight of compound of formula (I), the remainder of the composition consisting of one or more solid carriers and one or more surfactants.

32. The composition according to claim 29, which is an emulsifiable concentrate comprising from about 5 to about 30% by weight of compound of formula (I) and from about 5 to about 20% by weight of one or more emulsifiers, the remainder of the composition consisting of one or more solid carriers.

33. The composition according to claim 29, which is a flowable comprising from about 5 to about 50% by weight of compound of formula (I) and from about 3 to about 10% by weight of one or more dispersion wetting agents, the remainder of the composition consisting of water.

34. The method according to claim 5, wherein, in the compound of formula (I):

$R^1$ is $C_3$–$C_4$ branched alkyl, phenyl, or phenyl substituted by halogen or lower alkyl;

$R^3$ is phenyl or 2-naphthyl, each of which is unsubstituted or is substituted by one or two halogen, lower haloalkyl or lower haloalkoxy;

$R^4$ is methyl; and $R^5$ is methyl.

35. The method according to claim 34, wherein the compound of formula (I) has the formula:

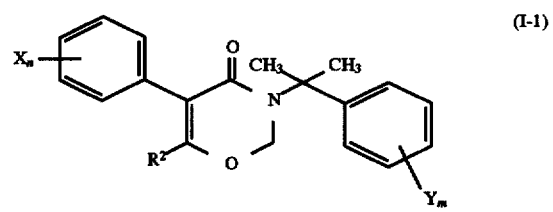

wherein:

X is halogen or lower alkyl;

Y is halogen or lower haloalkyl;

n is 0 or 1; and m is 0, 1 or 2, provided that when m is 2, then the substituents represented by Y can be the same or different.

36. A method for controlling the growth of weeds at a locus comprising applying to said weeds or to the locus in which they grow a herbicidally effective amount of a composition as claimed in claim 24.

37. The method according to claim 2, wherein the locus to which said compound is applied is farming land.

38. The method according to claim 37, wherein said farming land comprises paddy fields or upland fields.

39. The method according to claim 2, wherein the locus to which said compound is applied is non-farming land.

40. The method according to claim 2, wherein said compound is applied to said locus prior to germination of weeds.

41. The method according to claim 2, wherein said compound is applied to said weeds or the locus in which they grow at a stage of growth from pre-germination to growing.

42. The method according to claim 2, wherein said compound is applied at a rate of between about 0.1 and about 10,000 g/ha.

43. The method according to claim 42, wherein said compound is applied at a rate of between about 1 and about 5,000 g/ha.

44. The method according to claim 2, wherein said compound is applied to a crop-growing area in which the crop which has been planted or which is to be planted is paddy field rice, soybean, cotton, sugar beet, rape, sunflower, maize, upland rice or wheat.

45. The method according to claim 2, wherein said compound is applied to orchards, mulberry fields, turf or non-farming land.

46. A compound having the formula:

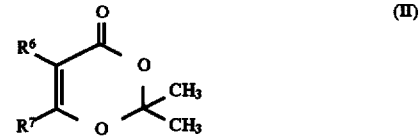

wherein:

$R^6$ is an aryl radical which is unsubstituted or is substituted; and $R^7$ is hydroxymethyl, acetyloxymethyl or formyl.

47. The compound according to claim 46 wherein $R^6$ is an aryl radical which is phenyl or naphthyl, each of which is unsubstituted or is substituted by one or more members selected from the group consisting of halogen, lower alkyl, lower alkoxy, lower haloalkyl, lower haloalkoxy and nitro.

48. A process for the preparation of a compound as claimed in claim 1, said process comprising reacting a compound of the formula

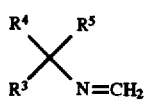

with a compound of the formula

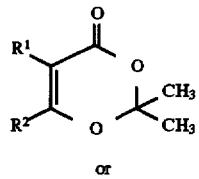

or

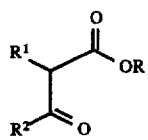

49. The process according to claim 48, wherein the reactants are employed in the amount of from about 0.5 to about 2 moles of compound of formula (III) per mole of compound of formula (II') or (IV).

50. The process according to claim 49, wherein the reactants are employed in the amount of from about 0.9 to abut 1.1 moles of compound of formula (III) per mole of compound of formula (II') or (IV).

51. A process for the preparation of a compound of formula (I) as claimed in claim 43 wherein $R^2$ is hydroxymethyl, lower alkoxymethyl, formyl, hydroximinomethyl, lower alkoxyiminomethyl, lower acyloxyiminomethyl or cyano, said process comprising:

(a) converting a compound of formula (I) wherein $R^2$ is acetyloxymethyl to the corresponding compound of formula (I) wherein $R^2$ is hydroxymethyl;

(b) converting a compound of formula (I) wherein $R^2$ is hydroxymethyl to the corresponding compound of formula (I) wherein $R^2$ is lower alkoxymethyl;

(c) converting a compound of formula (I) wherein $R^2$ is hydroxymethyl to the corresponding compound of formula (I) wherein $R^2$ is formyl;

(d) converting a compound of formula (I) wherein $R^2$ is formyl to the corresponding compound of formula (I) wherein $R^2$ is hydroxyiminomethyl;

(e) converting a compound of formula (I) wherein $R^2$ is hydroxyiminomethyl to the corresponding compound of formula (I) wherein $R^2$ is lower alkoxyiminomethyl;

(f) converting a compound of formula (I) wherein $R^2$ is hydroxyiminomethyl to the corresponding compound of formula (I) wherein $R^2$ is lower acyloxyiminomethyl; or (g) converting a compound of formula (I) wherein $R^2$ is hydroxyiminomethyl to the corresponding compound of formula (I) wherein $R^2$ is cyano.

* * * * *